United States Patent
Baichwal et al.

(10) Patent No.: US 9,351,938 B2
(45) Date of Patent: *May 31, 2016

(54) SUSTAINED RELEASE FORMULATION OF NALBUPHINE

(71) Applicant: Endo Pharmaceuticals Inc., Malvern, PA (US)

(72) Inventors: Anand R. Baichwal, Wapppingers Falls, NY (US); Philip A. Goliber, Lasne (BE); Anthony E. Carpanzano, New Milford, CT (US); Thomas Sciascia, Belmont, MA (US); Donald Diehl, II, New Fairfield, CT (US); Brian Vogler, North White Plains, NY (US); David Verbel, New York, NY (US); Stanley Au, Bethesda, MD (US)

(73) Assignee: ENDO PHARMACEUTICALS INC, Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/290,413

(22) Filed: May 29, 2014

(65) Prior Publication Data

US 2014/0271852 A1    Sep. 18, 2014

Related U.S. Application Data

(63) Continuation of application No. 13/773,136, filed on Feb. 21, 2013, now Pat. No. 8,765,175, which is a continuation of application No. 12/154,496, filed on May 23, 2008, now Pat. No. 8,394,812, which is a (Continued)

(51) Int. Cl.
*A61K 9/24* (2006.01)
*A61K 9/28* (2006.01)

(Continued)

(52) U.S. Cl.
CPC ........... *A61K 9/28* (2013.01); *A61K 9/0002* (2013.01); *A61K 9/205* (2013.01); *A61K 9/209* (2013.01); *A61K 9/2009* (2013.01); *A61K 9/2018* (2013.01); *A61K 9/2054* (2013.01); *A61K 9/2077* (2013.01); *A61K 31/485* (2013.01)

(58) Field of Classification Search
None
See application file for complete search history.

(56) References Cited

U.S. PATENT DOCUMENTS

| 4,237,140 A | 12/1980 | Dudzinski |
| 4,282,215 A | 8/1981 | Dudzinski et al. |

(Continued)

FOREIGN PATENT DOCUMENTS

| EP | 0 615 756 A1 | 9/1994 |
| EP | 0 615 756 B1 | 9/1994 |

(Continued)

OTHER PUBLICATIONS

Yang et al, Intl. J of Pharmaceutics 220 (2001) pp. 91-99.

(Continued)

*Primary Examiner* — Benjamin Packard
(74) *Attorney, Agent, or Firm* — Davidson, Davidson & Kappel LLC

(57) ABSTRACT

Sustained release formulations of nalbuphine or pharmaceutically acceptable salts thereof; methods for making the sustained release formulations of nalbuphine or pharmaceutically acceptable salts thereof; and methods for using the sustained release formulations of nalbuphine or pharmaceutically acceptable salts thereof to treat patients suffering from pain are provided.

24 Claims, 5 Drawing Sheets

Related U.S. Application Data continuation-in-part of application No. 11/509,347, filed on Aug. 24, 2006, now Pat. No. 8,771,732.

(60) Provisional application No. 60/772,466, filed on Feb. 10, 2006, provisional application No. 60/710,772, filed on Aug. 24, 2005.

(51) Int. Cl.
*A61K 9/00* (2006.01)
*A61K 9/20* (2006.01)
*A61K 31/485* (2006.01)

(56) References Cited

U.S. PATENT DOCUMENTS

| | | |
|---|---|---|
| 4,402,962 A | 9/1983 | Schmidt |
| 4,404,208 A | 9/1983 | Schmidt |
| 4,404,209 A | 9/1983 | Schmidt |
| 4,404,210 A | 9/1983 | Schmidt |
| 4,404,211 A | 9/1983 | Schmidt |
| 4,407,804 A | 10/1983 | Schmidt |
| 4,407,805 A | 10/1983 | Schmidt |
| 4,720,384 A | 1/1988 | Di Luccio et al. |
| 4,952,402 A | 8/1990 | Sparks et al. |
| 5,013,740 A | 5/1991 | Glover |
| 5,028,612 A | 7/1991 | Glover |
| 5,399,358 A | 3/1995 | Baichwal et al. |
| 5,750,534 A | 5/1998 | Yoa-Pu et al. |
| 5,958,452 A | 9/1999 | Oshlack et al. |
| 5,965,161 A | 10/1999 | Oshlack et al. |
| 5,968,551 A | 10/1999 | Oshlack et al. |
| 6,225,321 B1 | 5/2001 | Hu et al. |
| 6,261,599 B1 | 7/2001 | Oshlack et al. |
| 6,284,274 B1 | 9/2001 | Merrill et al. |
| 6,294,195 B1 | 9/2001 | Oshlack et al. |
| 6,335,033 B2 | 1/2002 | Oshlack et al. |
| 6,372,254 B1 | 4/2002 | Ting et al. |
| 6,437,000 B1 | 8/2002 | Mulye |
| 6,475,493 B1 | 11/2002 | Mulye |
| 6,525,062 B2 | 2/2003 | Levine |
| 6,602,521 B1 | 8/2003 | Ting et al. |
| 6,692,771 B2 | 2/2004 | Pather et al. |
| 6,706,281 B2 | 3/2004 | Oshlack et al. |
| 6,730,321 B2 | 5/2004 | Ting et al. |
| 6,743,442 B2 | 6/2004 | Oshlack et al. |
| 6,806,294 B2 | 10/2004 | Wimmer et al. |
| 6,923,988 B2 | 8/2005 | Patel et al. |
| 2002/0016331 A1 | 2/2002 | Levine |
| 2002/0058050 A1 | 5/2002 | Sackler et al. |
| 2002/0176888 A1 | 11/2002 | Bartholomaeus et al. |
| 2003/0035837 A1 | 2/2003 | Sackler et al. |
| 2003/0077306 A1 | 4/2003 | Pather et al. |
| 2003/0105120 A1 | 6/2003 | Hu et al. |
| 2003/0180361 A1 | 9/2003 | Oshlack et al. |
| 2003/0203028 A1 | 10/2003 | Ting et al. |
| 2003/0211157 A1 | 11/2003 | Simon |
| 2004/0081694 A1 | 4/2004 | Oshlack et al. |
| 2004/0121001 A1 | 6/2004 | Oshlack et al. |
| 2004/0161382 A1 | 8/2004 | Yum et al. |
| 2004/0185096 A1 | 9/2004 | Oshlack et al. |
| 2004/0204434 A1 | 10/2004 | Shafer et al. |
| 2004/0224020 A1 | 11/2004 | Schoenhard |
| 2005/0074493 A1 | 4/2005 | Mehta et al. |
| 2005/0089568 A1 | 4/2005 | Oshlack et al. |
| 2005/0165038 A1 | 7/2005 | Gordon |
| 2005/0169990 A1 | 8/2005 | Kao et al. |
| 2005/0176790 A1 | 8/2005 | Bartholomaus et al. |
| 2005/0222135 A1 | 10/2005 | Buschmann et al. |
| 2006/0111382 A1 | 5/2006 | Shafer et al. |

FOREIGN PATENT DOCUMENTS

| | | |
|---|---|---|
| EP | 1 149 836 A1 | 10/2001 |
| WO | WO9614058 | 5/1996 |
| WO | WO-01/22940 A1 | 4/2001 |
| WO | WO-01/93852 A2 | 12/2001 |
| WO | WO-2004/012715 A1 | 2/2004 |

OTHER PUBLICATIONS

European Search Report issued for European Appl. No. 11178912, dated Nov. 24, 2011 (2 pages).

Aungst, B.J. et al., "Oral and Recal Nalbuphine Bioavailability: First-Pass Metabolism in Rats and Dogs," Biopharm. & Drug Disp., vol. 6: 413-421 (1985).

Hoskin, P.J. and Hanks, G.W., "Opioid Agonist-Antagonist Drugs in Acute and Chronic Pain States," Drugs, 41(3): 326-344 (1991).

International Search Report for PCT/US2006/033011, malled Oct. 29, 2007, 6 pages.

Yen, S.Y. et al., "Controlled Release of Nalbuphine Propionate from Biodegradable Microspheres: in vitro and in vivo studies", International Journal of Pharmaceutics, vol. 220, pp. 91-99, 2001.

Aitkenhead, A.R. et al., "The pharmacokientcis of oral and intravenous nalbuphine in healthy volunteers", *Br. J. Clin. Pharmac.*, vol. 25, pp. 264-268, 1988.

Alibeu, J.P., "Clinical application of nalpuphine", *Douleur Analgesia* (Switzerland), vol. 10, No. 4, pp. 139-146, 1997.

Beaver, WT et al., "Analgesic Effect of Intramuscular and Oral Nalbuphine in Postoperative Pain", *Clin. Pharmacol. Ther.*, vol. 29, pp. 174-180, Feb. 1981.

Bessard, G. et al., "Pharmacokinetics of intrarectal nalbuphine in children undergoing general anaesthesia", *Fundam. Clin. Pharmacol.*, vol. 11, No. 2, pp. 133-137, 1997.

Cooper, SA et al., "A model to evaluate mild analgesics in oral surgery outpatients", *Clin. Pharmacol. Ther.*, vol. 20, No. 2, pp. 241-250, 1976.

Cox, EH et al., "A population pharmacokinetc-pharmacodynamic analysis of repeated measures time-to=even pharmacodynamic responses: the antiemetic effect of ondansetron", *J. Pharmacokinet. Biopharm.*, vol. 27, No. 6, pp. 625-644, 1999.

Endo Pharmaceuticals, Inc., Nalbuphine (Nubain) Product Information 2003.

Errick, JK et al., "Nalbuphine: A Preliminary Review of its Pharmacological Properties and Therapeutic Efficacy", *Drugs*, vol. 26, No. 3, pp. 191-211, 1983.

Forbes, JA et al., "Nalbuphine, Acetaminophen, and their Combination in Postoperative Pain", *Clin. Pharmacol. Ther.*, vol. 35, pp. 843-851, Jun. 1984.

Jaillon, P. et al., "Pharmacokinetics of nalbuphine in infants, young healthy volunteers, and elderly patients," *Clin. Pharmacol. Ther.*, vol. 46, No. 2, pp. 226-233, 1989.

Jain, AK et al., "Comparison of Oral Nalbuphine, Acetaminophen, and their Combination in Postoperative Pain", *Clin. Pharmacol. Ther.*, vol. 39, pp. 295-299, Mar. 1986.

Kantor, TG et al., "Oral Nalbuphine in Postpartum Pain", *Clin. Pharmacol. Ther.*, vol. 35, No. 1, pp. 46-49, 1984.

Kay, B. et al., "Oral Nalbuphine for the Treatment of Pain after Dental Extractions", *Br. J. Anaesth.*, vol. 61, pp. 313-317, 1988.

Lo, Man-Wai et al., "The Disposition and Bioavailability of Intravenous and Oral Nalbuphine in Healthy Volunteers," *J. Clin. Pharmacol.*, vol. 27, pp. 866-873, 1987.

Mallinckrodt, "Nalbuphine hydrochloride", *Technical Package*, Apr. 10023.

Mandema, JW et al., "Population pharmacodynamic model for ketorolac analgesia", *Clin. Pharmacol. Ther.*, vol. 60, No. 6, pp. 619-635, Dec. 1996.

Martindale, "The complete drug reference", 33rd edition, The Pharmaceutical Press, London, UK, pp. 59-60, 2002.

McKenzie, J.E. et al., "Nalbuphine's reversal of hypovolemic shock in the anesthetized rat", *Circulatory Shock*, vol. 17, No. 1, pp. 21-33, 1985.

Mehlisch, D. et al., "Comparisons between dental and non-dental model responses to predict a non-dental model response", *APS Abstract*, 2003.

Merck Index Record on Nalbuphine, "Nalbuphine Phisical/Chemical Properties/Formulation", Merck & Co., Inc., 2003.

(56) References Cited

OTHER PUBLICATIONS

Nalbuphine Hydrochloride. Micromedex vol. 20: Health Series Integrated Index 2004 (including DRUGDEX, Physician's Desk Reference, and Martindale—The Complete Drug Reference—Monographs) 2004.

Nicolle, E. et al., "Therapeutic monitoring of nalbuphine: transplacental transfer and estimated pharmacokinetics in the neonate", *European Journal of Clinical Pharmacology* (Germany), vol. 49, No. 6, pp. 485-485, 1996.

Okun, R., "Analgesic Effects of Oral Nalbuphine and Codeine in Patients with Postoperative Pain", *Clin. Pharmacol. Ther.*, vol. 32, pp. 517-524, Oct. 1982.

Orange Book Query. Available on line at http://www/fda.gov/cder/ob/default.htm.

Physicians Desk Reference, 57th edition, Thomson PDR, Montvale, NJ, pp. 1302-1303, 2003.

Quarry, M.A. et al., "Determination of nalbuphine HCl, methylparaben, and propy[araben in nalbuphine HCl injection by high performance liquid chromatography", *Chromatographia*, vol. 47, No. 9/10, pp. 515-522, May 1998.

Sheiner, LB et al., "Analysis of nonrandomly censored ordered categorical longitudinal data from analgesic trials", *J. Am. Stat. Assoc.*, vol. 92, No. 440, pp. 1235-1244, Dec. 1997.

Sheiner, LB, "A new approach to the analysis of analgesic drug trials, illustrated with bromfenac data", *Clin. Pharmacol. Ther.*, vol. 56, No. 3, pp. 309-322, Sep. 1994.

Stambaugh, JE, Jr., "Evaluation of nalbuphine: Efficacy and safety in the management of chronic pain associated with advanced malignancy", *Current Therapeutic Research—Clinical and Experimental*, vol. 31, No. 3, pp. 393-401, Mar. 1982.

Sunshine, A. et al., "A Study of the Analgesic Efficacy of Nalbuphine in Post-Partum Pain", *Curr. Ther. Res.*, vol. 33, No. 1, pp. 108-114, Jan. 1983.

Walker, DJ et al., "Subjective, Psychomotor, and Physiological Effects of Cumulative Doses of Opioid µ Agonists in Healthy Volunteers", *JPET*, vol. 289, No. 3, pp. 1454-1464, 1999.

Wang, D. et al., "Comparative population pharmacokinetic pharmacodynamic analysis for piroxicam-beta-cyclodextrin and piroxicam", *J. Clin. Pharmacol.*, vol. 40, No. 11, pp. 1257-1266, 2000.

Wilson, SJ et al., "Pharmacokinetics of nalbuphine during parturition", *American Journal of Obstetrics and Gynecology* (United States), vol. 155, No. 2, pp. 340-344, Aug. 1986.

Woollard, M. et al., "Hitting them where it hurts? Low dose nalbuphine therapy", *Emergency Medicine Journal—EMJ* (England), vol. 19, No. 6, pp. 565-570, Nov. 2002.

Examiner's Search Report issued in corresponding Canadian Application No. 2,881,739, dated Dec. 9, 2015.

SUSTAINED RELEASE FORMULATION OF NALBUPHINE

CROSS-REFERENCE TO RELATED APPLICATIONS

This application is a continuation of U.S. patent application Ser. No. 13/773,136, filed Feb. 21, 2013, which is a continuation of U.S. Pat. No. 8,394,812, filed May 23, 2008, which is a continuation-in-part of U.S. patent application Ser. No. 11/509,347, filed on Aug. 24, 2006, which claims the benefit of U.S. Provisional Patent Application No. 60/772,466, filed Feb. 10, 2006 and U.S. Provisional Patent Application No. 60/710,772, filed on Aug. 24, 2005, the disclosures of which are hereby incorporated by reference in their entirety.

FIELD OF THE INVENTION

The invention provides sustained release formulations of nalbuphine and pharmaceutically acceptable salts thereof; methods for making the sustained release formulations of nalbuphine and pharmaceutically acceptable salts thereof; and methods for using the sustained release formulations of nalbuphine and pharmaceutically acceptable salts thereof to treat patients suffering from pain.

BACKGROUND OF THE INVENTION

Pain is the most frequently reported symptom and it is a common clinical problem that confronts the clinician. Many millions of people in the United States suffer from pain that is chronically undertreated or inappropriately managed. The clinical usefulness of the analgesic properties of opioids has been recognized for centuries, and morphine and its derivatives have been widely used for analgesia for decades in a variety of clinical pain states.

Nalbuphine HCl (17-(cyclobutylmethyl)-4,5α-epoxymorphinan-3,6α,14-triol hydrochloride) is a synthetic opioid agonist-antagonist analgesic belonging to the phenanthrene class of opioids. Nalbuphine is related to the opioid antagonist, naloxone, and also to the opioid analgesic, oxymorphone. Nalbuphine HCl is marketed in the United States as an injectable product and is primarily a kappa agonist/partial mu antagonist analgesic.

Although oral administration of nalbuphine has been studied (Lo, M W et al. The Disposition and Bioavailability of Intravenous and Oral Nalbuphine in Healthy Volunteers, *J. Clin. Pharmacol.* 27:866-873 (1987); Aitkenhead, A R et al. "The Pharmacokinetics of Oral and Intravenous Nalbuphine in Healthy Volunteers", *Br. J. Clin. Pharmacol.* 25:264-288 (1988); Jaillon P, et al. Pharmacokinetics of Nalbuphine in Infants, Young Healthy Volunteers, and Elderly Patients, *Clin. Pharmacol. Ther.* 46:226-233 (1989)), it has never received marketing approval. Currently, nalbuphine is marketed only as an injection (10 mg/ml in 10 ml multiple dose vials; 20 mg/ml in 10 ml multiple dose vials; 10 mg/ml in 1 ml ampules; 20 mg/ml in 1 ml ampules) for intramuscular, subcutaneous, and intravenous administration.

The dosing interval of nalbuphine injection is approximately every three to six hours. Although the half-life following oral administration of immediate release nalbuphine has been reported to be somewhat longer (approximately five to seven hours), the drug effect generally wears off toward the end of the therapeutic window (e.g., dosing interval).

SUMMARY OF THE INVENTION

The invention provides compositions including nalbuphine or a pharmaceutically acceptable salt thereof and a sustained release delivery system. The sustained release delivery system includes at least one hydrophilic compound, at least one cross-linking agent and at least one pharmaceutical diluent. The sustained release delivery system may further include one or more additional cross-linking compounds.

The invention also provides compositions including nalbuphine or a pharmaceutically acceptable salt thereof and a sustained release delivery system. The sustained release delivery system includes at least one hydrophilic compound, at least one cationic cross-linking compound, and at least one pharmaceutical diluent. The sustained release delivery system may further include one or more additional cross-linking compounds.

In certain preferred embodiments, the composition is a monolithic dosage form, such as a monolithic tablet.

In certain embodiments, the invention further provides multilayer compositions including nalbuphine or a pharmaceutically acceptable salt thereof and a sustained release delivery system. The formulation includes a first layer and a second layer. The first layer includes an immediate release formulation of nalbuphine hydrochloride or a pharmaceutically acceptable salt thereof, while the second layer includes an extended release formulation of nalbuphine or a pharmaceutically acceptable salt of nalbuphine. In this aspect, the first layer includes nalbuphine or a pharmaceutically acceptable salt of nalbuphine and the second layer includes nalbuphine or a pharmaceutically acceptable salt of nalbuphine and a sustained release delivery system. The first layer optionally includes a sustained release delivery system. In one embodiment, the second layer includes about 45 mg nalbuphine or a pharmaceutically acceptable salt of nalbuphine and about 110 mg to about 150 mg of a sustained release delivery system; and the first layer includes from about 10 mg to about 20 mg nalbuphine or a pharmaceutically acceptable salt of nalbuphine and, optionally, about 3 mg to about 19 mg of a sustained release delivery system. In another embodiment, the second layer includes about 45 mg nalbuphine or a pharmaceutically acceptable salt of nalbuphine and about 110 mg to about 150 mg of a sustained release delivery system; and the first layer includes from about 10 mg to about 20 mg nalbuphine or a pharmaceutically acceptable salt of nalbuphine. In this embodiment, the first layer does not include a sustained release delivery system. In some embodiments, the sustained release delivery system includes about 12% to 42% by weight locust bean gum, about 8% to about 28% by weight xanthan gum, about 20% to about 70% by weight mannitol and about 5% to about 20% by weight calcium sulfate dihydrate.

In one aspect, the invention provides an oral unit dosage form including nalbuphine or a pharmaceutically acceptable salt thereof. The oral dosage form provides an analgesic effect over a period of at least about 12 hours. In some embodiments, the oral dosage form provides a blood serum level of nalbuphine characterized by one or more peaks followed by a plateau region. In some embodiments, the oral dosage form is characterized in that 75-100% of the nalbuphine is released after about 12 hours as determined using USP Apparatus III at 15 dpm in a pH 6.8 buffer at 37° C.

In one aspect, the invention provides an oral unit dosage form of a medicament including a uniform dosage of nalbuphine; and a sustained release delivery system. The oral unit dosage form is characterized in that nalbuphine is released in one or more peaks followed by a plateau region.

In yet another aspect of the invention, there is provided a sustained release oral solid dosage form comprising a therapeutically effective amount of nalbuphine or a pharmaceutically acceptable salt thereof in a sustained release delivery system, wherein the dosage form provides a mean $T_{max}$ about 1.77 (±1.539) to about 8.01 (±2.196) hours after oral administration to human subjects and maintains a plateau of a relatively constant blood serum level of nalbuphine which does not consistently increase or decrease from time point to time point.

In another aspect of the invention, there is provided a sustained release oral solid dosage form comprising a therapeutically effective amount of nalbuphine or a pharmaceutically acceptable salt thereof in a sustained release delivery system, wherein the plateau has a duration of about 1 hours to about 12 hours; about 2 hours to about 10 hours, or about 6 hours to about 9 hours. In other words, when the plateau begins after oral administration it lasts at least about 1 hour and, on the other hand, can last as long as about 12 hours.

In yet another aspect of the invention, there is provided a sustained release oral solid dosage form comprising a therapeutically effective amount of nalbuphine or a pharmaceutically acceptable salt thereof in a sustained release delivery system, wherein the dosage form provides a mean $C_{max}$ of about 7 to about 16 ng/ml. In certain embodiments, the mean $C_{max}$ is about 8.58 ng/ml (±4.217) based on a 60 mg single dose; about 7.17 ng/ml (±3.175) based on a 60 mg single dose; about 7.920 ng/ml (±1.4722) based on a 60 mg single dose; and about 7.750 ng/ml (±6.034) based on a 60 mg single dose.

In certain other embodiments, the mean $C_{max}$ is about 12.87 ng/ml (±4.031) based on a 120 mg single dose; about 14.1 ng/ml (±6.23) based on a 120 mg single dose; about 11.3 ng/ml (±7.17) based on a 120 mg single dose; about 13.4 ng/ml (±8.81) based on a 120 mg single dose; about 14.2 ng/ml (±8.87) based on a 120 mg single dose; about 12.5 ng/ml (±8.02) based on a 120 mg single dose; about 15.574 ng/ml (±8.4070) based on a 120 mg single dose; about 12.498 ng/ml (±7.1308) based on a 120 mg single dose; about 12.903 ng/ml (±5.4062) based on a 120 mg single dose; about 12.700 ng/ml (±5.7697) based on a 120 mg single dose; and about 13.265 ng/ml (±6.458) based on a 120 mg single dose.

In yet another embodiment, the mean $C_{max}$ is about 15.59 ng/ml (±8.379) based on a 180 mg single dose.

In another aspect of the invention, the dosage forms described herein provide a width at 50% of the height of the plasma concentration curve/time curve of nalbuphine about 10 hours based on a 60 mg single dose; or about 13 hours based on a 60 mg single dose.

In another aspect of the invention, the dosage forms described herein provide a width at 50% of the height of the plasma concentration curve/time curve of nalbuphine about 17 hours based on a 120 mg single dose.

In another aspect of the invention, the dosage forms described herein provide a width at 50% of the height of the plasma concentration curve/time curve of nalbuphine about 12 hours based on a 180 mg single dose.

In another aspect, the present invention is also directed to a method of treating pain in a human in need thereof, comprising administering an oral solid dosage form comprising a therapeutically effective amount of nalbuphine or a pharmaceutically acceptable salt thereof in a sustained release delivery system, wherein the dosage form provides a mean $T_{max}$ at about 1.77 (±1.539) to about 8.01 (±2.196) hours after oral administration to human subjects and maintains a plateau of a relatively constant blood serum level of nalbuphine which does not consistently increase or decrease from time point to time point.

The invention also provides methods for treating pain in patients by administering an effective amount of any of the compositions of the invention. The pain may be mild, moderate or severe. In some embodiments, the pain may be mild to moderate or moderate to severe. The pain may be acute pain, chronic pain, nociceptive pain, neuropathic pain, visceral pain, or idiopathic pain.

The invention also provides methods for making such compositions.

These and other aspects of the invention are described in detail herein.

BRIEF DESCRIPTION OF THE DRAWINGS

A more complete appreciation of the invention and many of its advantages will be understood by reference to the description of the invention when considered in connection with the following drawings, which are presented for the purpose of illustration only and are not intended to be limiting and in which.

DETAILED DESCRIPTION OF THE PREFERRED EMBODIMENTS

Figure 1:
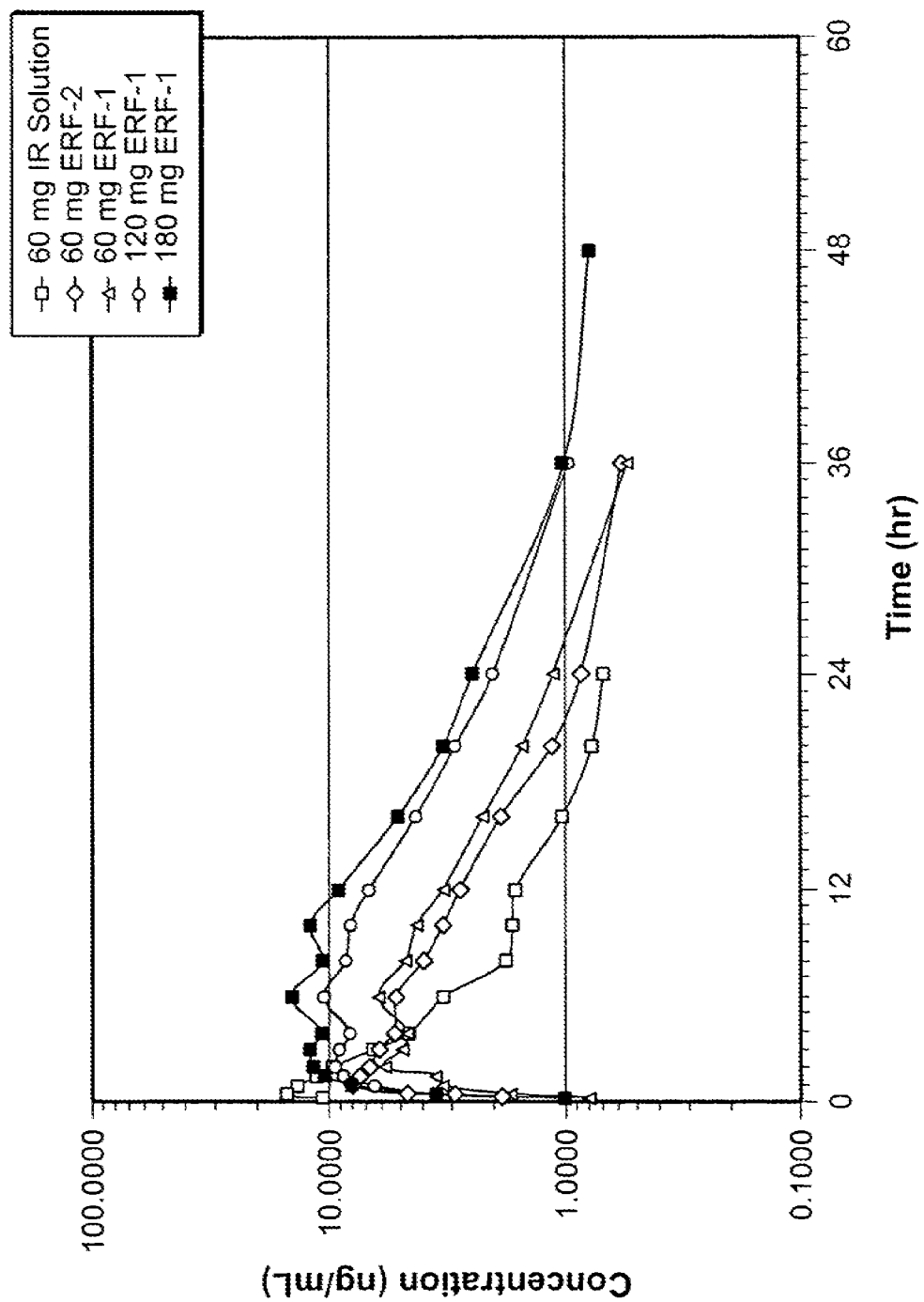
FIG. 1 is a graphical representation of the log of the mean nalbuphine plasma concentration versus time for numerous nalbuphine compositions described herein.
Figure 2:
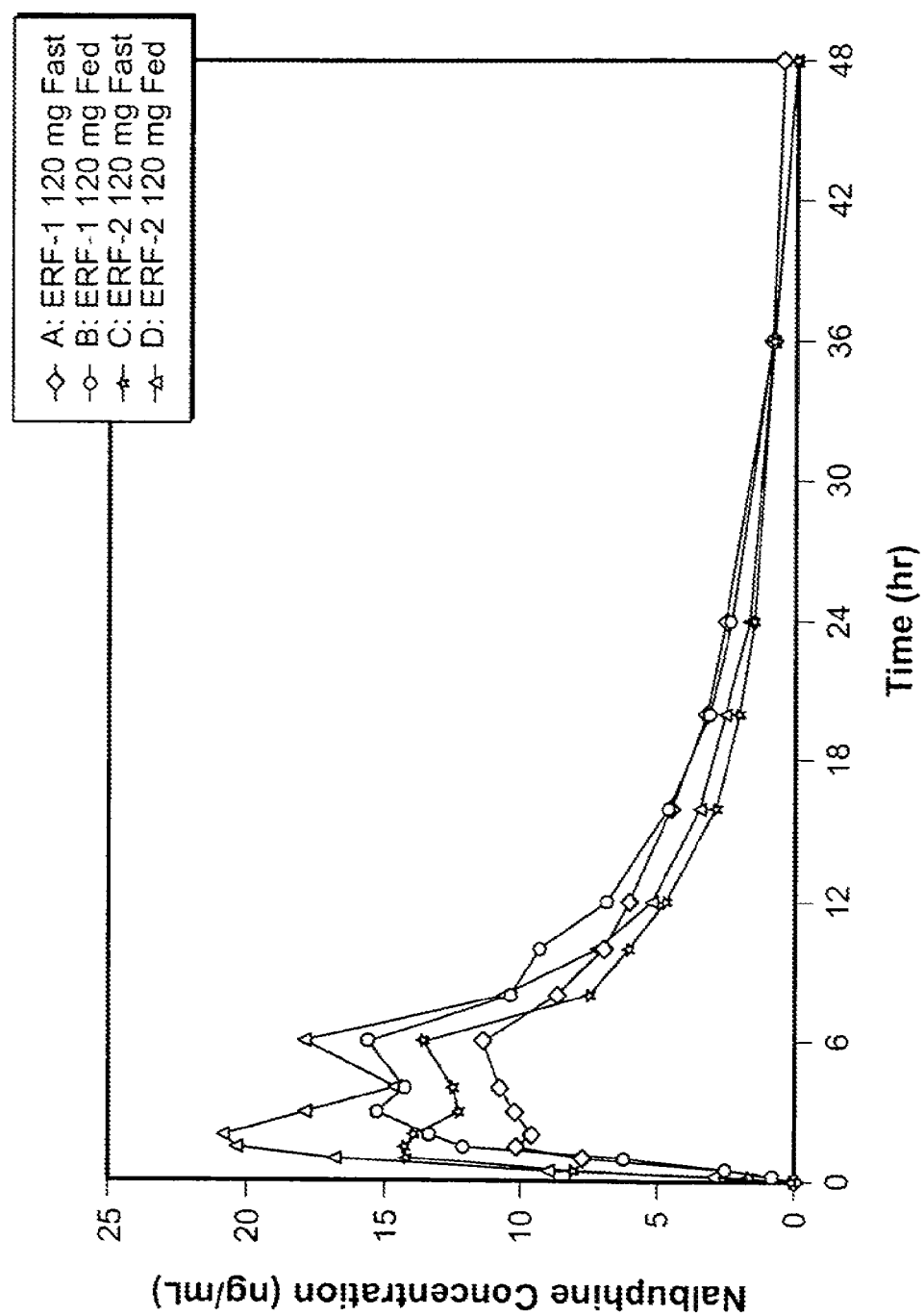
FIG. 2 is a graphical representation of the linear mean nalbuphine plasma concentration versus time for the study described in Example 30 below.
Figure 3:
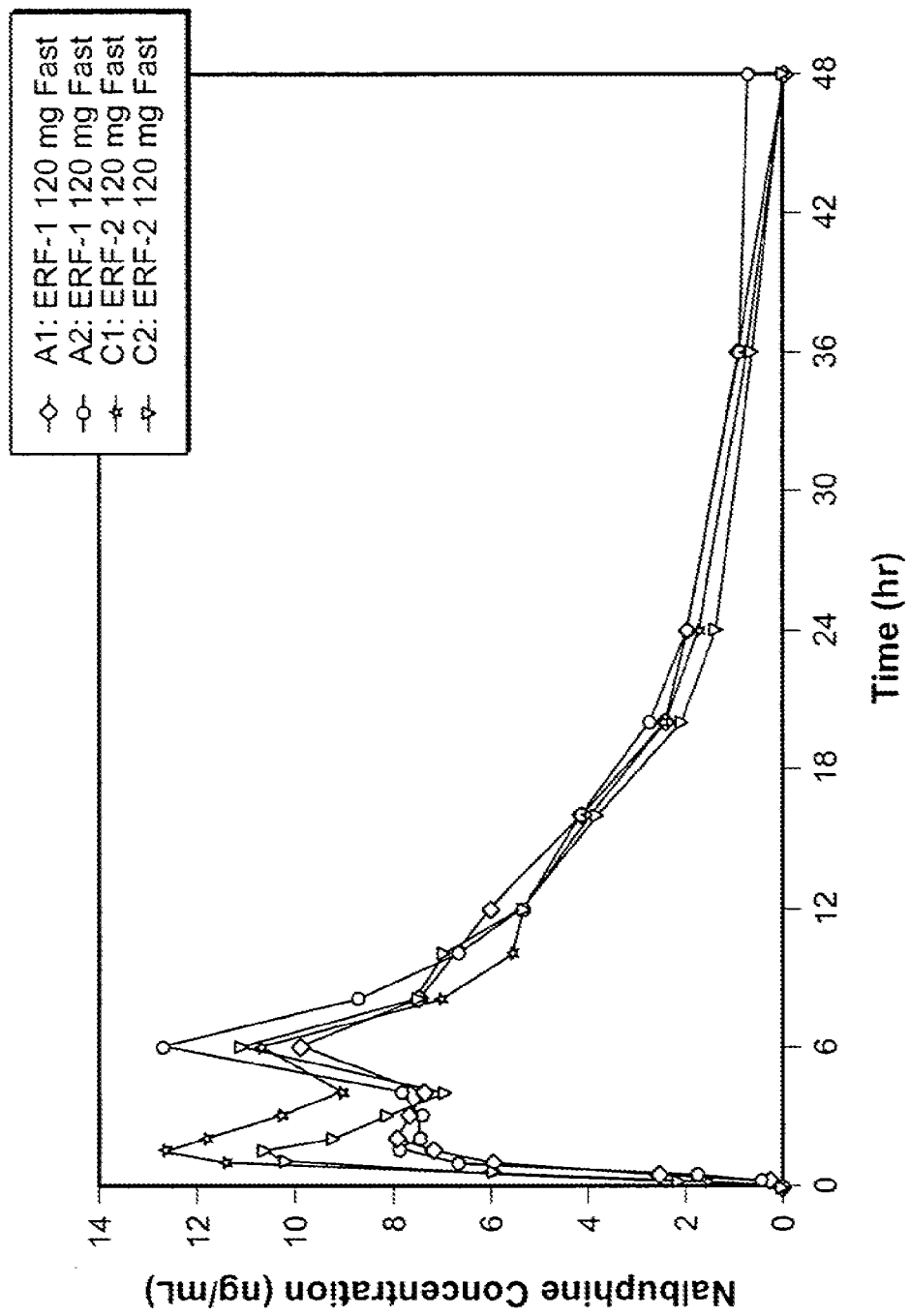
FIG. 3 is a graphical representation of the linear mean nalbuphine plasma concentration versus time for the study described in Example 31 below.
Figure 4:
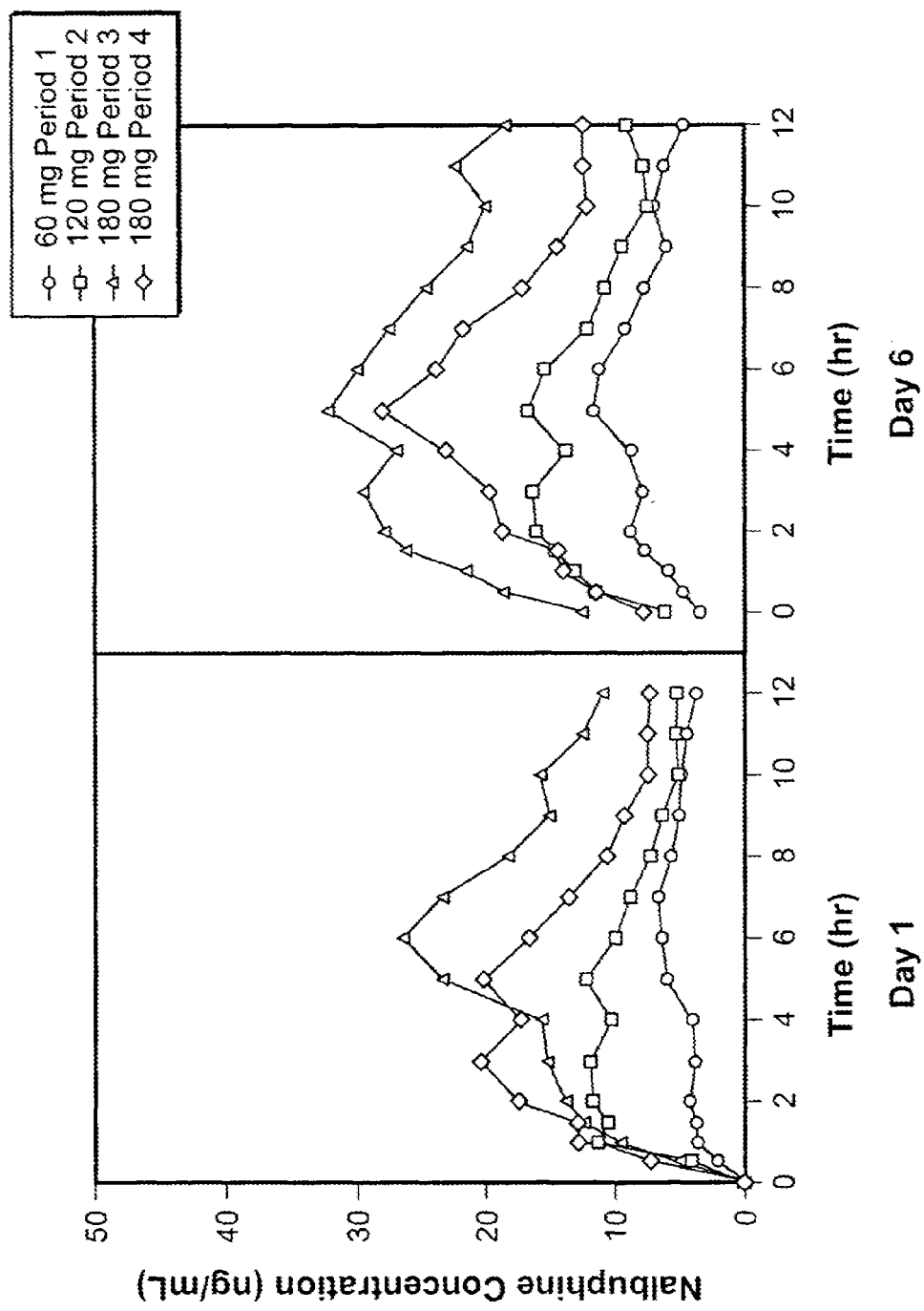
FIG. 4 is a graphical representation of the linear mean nalbuphine plasma concentration versus time for the study described in Example 32 below.
Figure 5:
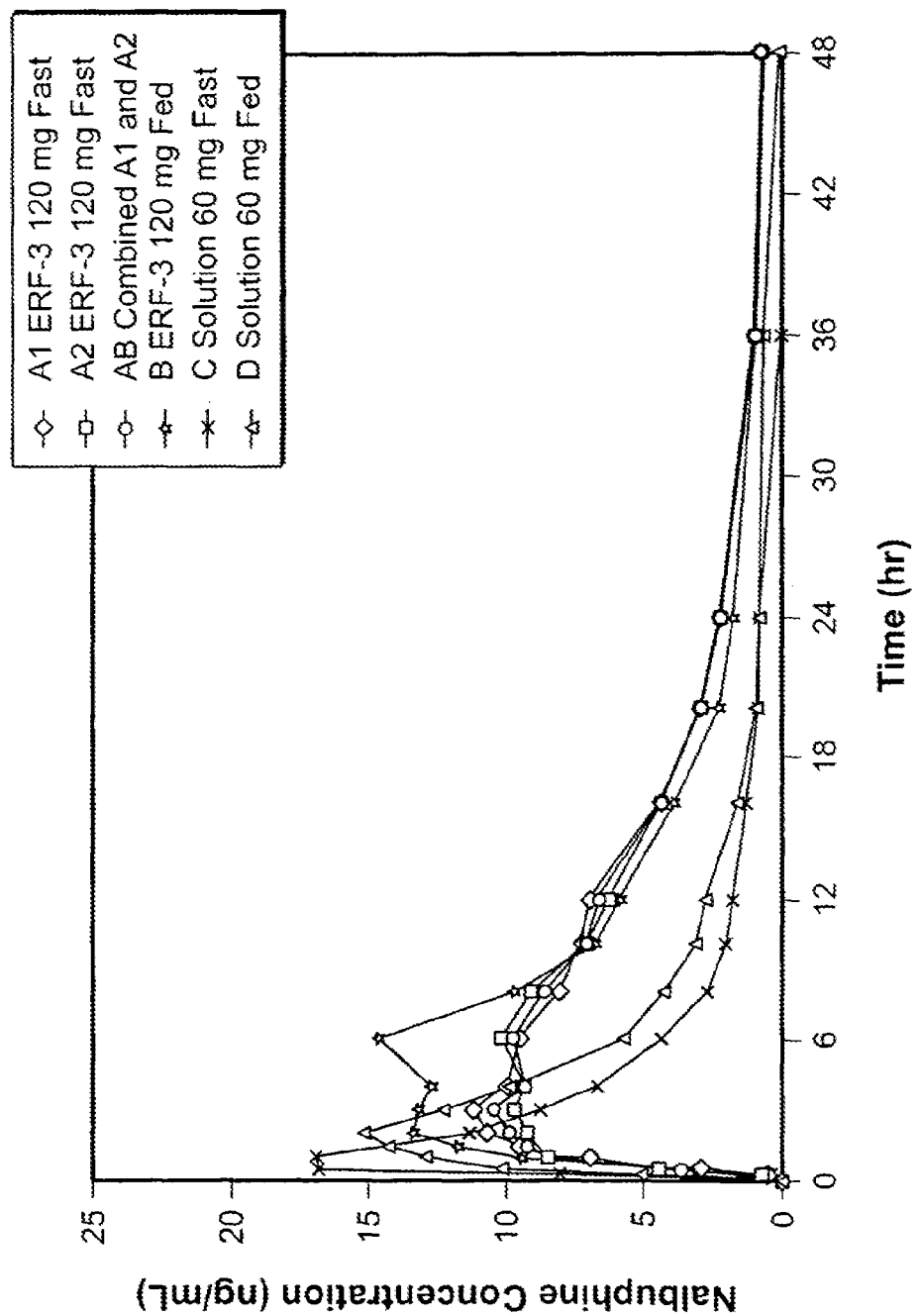
FIG. 5 is a graphical representation of the linear mean nalbuphine plasma concentration versus time for the study described in Example 33 below.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

The invention provides oral sustained release formulations of nalbuphine including an analgesically effective amount of nalbuphine or a pharmaceutically acceptable salt thereof. The oral sustained release formulations of the invention provide a controlled release of the drug over a longer period than observed for injectable or immediate release oral formulations (e.g., at least about 8-12 hours). Thus, by reducing the frequency of dosing, the invention provides the potential for enhanced patient convenience. The lower dosing frequency also has the potential to provide reduced side effects because the patient may be exposed to lower peak concentrations of drug over time.

The invention provides compositions including nalbuphine or a pharmaceutically acceptable salt thereof and a sustained release delivery system. The sustained release delivery system includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent.

The nalbuphine may be homogeneously dispersed in the sustained release delivery system. In some embodiments, the nalbuphine or pharmaceutically acceptable salt thereof is present in the composition in an amount of about 1 mg to about 200 mg; about 1 mg to about 150 mg; about 1 mg to about 125 mg; or about 1 mg to about 100 mg. In some embodiments, the nalbuphine or pharmaceutically acceptable salt thereof is present in the composition in an amount of about 5 mg to about 80 mg; about 10 mg to about 70 mg; about 15 mg to about 60 mg; about 40 mg to about 80 mg; about 50 mg to about 70 mg; or about 45 mg to about 60 mg. In one embodiment, the nalbuphine or pharmaceutically acceptable salt thereof is present in the composition in an amount of about 20 mg, about 40 mg, about 60 mg, about 75 mg, about 80 mg, about 100 mg, about 120 mg, about 140 mg, about 150 mg, about 160 mg, about 175 mg, about 180 mg or about 200 mg. In another embodiment, the nalbuphine or pharmaceutically acceptable salt thereof is present in the composition in an amount of about 45 mg.

In some embodiments, the sustained release delivery system is present in the composition in an amount from about 10 mg to about 420 mg; from about 25 mg to about 225 mg; from about 21 mg to about 198 mg; or from about 80 mg to about 200 mg; from about 80 mg to about 220 mg; from about 90 mg to about 210 mg; from about 100 mg to about 200 mg; from about 110 mg to about 190 mg; from about 120 mg to about 180 mg; from about 130 mg to about 170 mg; from about 140 mg to about 160 mg; from about 30 mg to about 60 mg; from about 60 mg to about 180 mg; from about 30 mg to about 180 mg, from about 75 mg to about 150 mg, from about 80 mg to about 160 mg, from about 90 mg to about 150 mg, from about 100 mg to about 140 mg, from about 110 mg to about 130 mg, from about 100 mg to about 300 mg, from about 200 mg to about 300 mg or from about 200 mg to about 250 mg. In one embodiment, the sustained release delivery system is present in the composition in an amount from about 75 mg to about 150 mg. In some embodiments, the sustained release delivery system is present in the composition in an amount of about 30 mg, about 60 mg, about 75 mg, about 80 mg, about 90 mg, about 100 mg, about 110 mg, about 112 mg, about 115 mg, about 117 mg, about 120 mg, about 125 mg, about 130 mg, about 135 mg, about 140 mg, about 145 mg, about 150 mg, about 160 mg, about 170 mg, about 180 mg, about 190 mg, about 200 mg, about 210 mg, about 220 mg, about 225 mg, about 230 mg, about 240 mg, about 250 mg, about 260 mg, about 270 mg, about 280 mg, about 300 mg, about 320 mg, about 340 mg, about 360 mg, about 380 mg, about 400 mg or about 420 mg. In another embodiment, the sustained release delivery system is present in the composition in an amount of about 112 mg. "Nalbuphine" includes nalbuphine, metabolites thereof, derivatives thereof, and/or pharmaceutically acceptable salts thereof. Metabolites of nalbuphine include, for example the glucuronide conjugate metabolite and metabolites resulting from methylation, oxidation/dehydrogenation, hydroxylation, double hydroxylation, triple hydroxylation, oxidative methylation, glucoside conjugation, glucuronide conjugation, and hydroxyl-glucuronide conjugation of nalbuphine. Isomers include the C-6β-epimer of nalbuphine (Mallinckrodt, Nalbuphine hydrochloride Technical Package August 2003).

In the compositions of the invention, the ratio of nalbuphine or pharmaceutically acceptable salt thereof to the sustained release delivery system is generally from about 4:1 to about 1:25. In some embodiments, the ratio of nalbuphine or pharmaceutically acceptable salt thereof to the sustained release delivery system is generally from about 2.5:1 to about 1:4. In some embodiments, the ratio of nalbuphine or pharmaceutically acceptable salt thereof to the sustained release delivery system is generally from about 5:1 to about 1:5, about 4:1 to about 1:4, about 3:1 to about 1:3, about 2:1 to about 1:2, about 1:1 to about 1:5, about 1:1 to about 1:4, about 1:1 to about 1:3, about 1:1 to about 1.2, and about 1:2 to about 1:3. In some embodiments, the ratio of nalbuphine or pharmaceutically acceptable salt thereof to the sustained release delivery system is about 1:1, about 1:2, about 1:2.5, about 1:3, about 1:4, or about 1:5.

In one embodiment, at least one hydrophilic compound is present in the sustained release delivery system in an amount of about 5% to about 80% by weight; the at least one cross-linking agent is present in the sustained release delivery system in an amount of about 0.5% to about 80% by weight; and the at least one pharmaceutical diluent is present in the sustained release delivery system in an amount of about 20% to about 80% by weight. In another embodiment, the at least one hydrophilic compound is present in the sustained release delivery system in an amount of about 8% to about 31% by weight; the at least one cross-linking agent is present in the sustained release delivery system in an amount of about 12% to about 47% by weight; and the at least one pharmaceutical diluent is present in the sustained release delivery system in an amount of about 20% to about 78% by weight. In another embodiment, the at least one hydrophilic compound is present in the sustained release delivery system in an amount of about 10% to about 20% by weight; the at least one cross-linking agent is present in the sustained release delivery system in an amount of about 15% to about 25% by weight; and the at least one pharmaceutical diluent is present in the sustained release delivery system in an amount of about 50% to about 85% by weight. In some embodiments, the at least one hydrophilic compound is present in the sustained release delivery system in an amount of about 8%, about 9%, about 10%, about 111%, about 12%, about 13%, about 14%, about 15%, about 16%, about 17%, about 18%, about 19%, about 20%, about 22%, about 24%, about 26%, about 28%, or about 30% by weight; the at least one cross-linking agent is present in the sustained release delivery system in an amount of about 10%, about 11%, about 12%, about 13%, about 14%, about 15%, about 16%, about 17%, about 18%, about 19%, about 20%, about 22%, about 24%, about 26%, about 28%, about 30%, about 32%, about 33%, about 34%, or about 35% by weight; and the at least one pharmaceutical diluent is present in the sustained release delivery system in an amount of about 40%, about 45%, about 50%, about 55%, about 60%, about 65%, about 70%, about 80%, or about 85% by weight. In some embodiments, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cross-linking agent is present in the sustained release delivery system in an amount of about 15%, about 16%, about 17%, about 18%, about 19%, about 20%, or about 22% by weight; and the at least one pharmaceutical diluent is present in the sustained release delivery system in an amount of about 55%, about 60%, about 65%, about 70%, about 80%, or about 85% by weight. In one embodiment, the at least one hydrophilic compound is present in the sustained release delivery system in an amount of about 8%, about 12%, or about 20% by weight; the at least one cross-linking agent is present in the sustained release delivery system in an amount of about 12%, about 18%, or about 30% by weight; and the at least one pharmaceutical diluent is present in the sustained release delivery system in an amount of about 40%, about 60%, or about 70% by weight.

In one embodiment, nalbuphine is in the form of any pharmaceutically acceptable salt known in the art. Exemplary pharmaceutically acceptable salts include without limitation hydrochloric, sulfuric, nitric, phosphoric, hydrobromic, maleric, malic, ascorbic, citric, tartaric, pamoic, lauric, stearic, palmitic, oleic, myristic, lauryl sulfuric, napthalinesulfonic, linoleic, linolenic acid, and the like. One embodiment includes the hydrochloride salt of nalbuphine.

The sustained release delivery system includes at least one hydrophilic compound. The hydrophilic compound preferably forms a gel matrix that releases the nalbuphine or the pharmaceutically acceptable salt thereof at a sustained rate upon exposure to liquids. The rate of release of the nalbuphine or the pharmaceutically acceptable salt thereof from the gel matrix depends on the drug's partition coefficient between the components of the gel matrix and the aqueous phase within the gastrointestinal tract. In the compositions of the invention, the weight ratio of nalbuphine to hydrophilic compound is generally in the range of about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, and about 2:1 to about 1:2. In some embodiments, the weight ratio of nalbuphine to hydrophilic compound is in the range of about 10:1 to about 1:1, about 10:1 to about 2:1, about 9:1 to about 1:1, about 8:1 to about 1:1, about 7:1 to about 1:1, about 6:1 to about 1:1, about 5:1 to about 1:1, about 4:1 to about 1:1, about 3:1 to about 1:1, and about 2:1 to about 1:1. In some embodiments, the weight ratio of nalbuphine to hydrophilic compound is in the range of about 6:1 to about 1:1, about 5:1 to about 2:1, about 4:1 to about 3:1, about 4:1 to about 2:1, and about 5:1 to about 2:1. In some embodiments, the weight ratio of nalbuphine to hydrophilic compound is about 5:1, about 4.5:1, about 4.4:1, about 4:1, about 3.5:1, about 3.3:1, about 3:1, about 2.5:1, and about 2:1.

The sustained release delivery system generally includes the hydrophilic compound in an amount of about 5% to about 80% by weight. In some embodiments, the sustained release delivery system generally includes the hydrophilic compound in an amount of about 5% to about 30%, about 8% to about 31%, about 10% to about 20%, about 20% to about 60%, or about 40% to about 60% by weight. In one embodiment, the sustained release delivery system includes the hydrophilic compound in an amount of about 8% to about 31% by weight. In one embodiment, the sustained release delivery system includes the hydrophilic compound in an amount of about 10% to about 20% by weight. In some embodiments, the sustained release delivery system includes the hydrophilic compound in an amount of about 10%, about 11%, about 12%, about 13%, about 14%, about 15%, about 16%, about 17%, about 18%, about 19%, or about 20% by weight. In one embodiment, the sustained release delivery system includes the hydrophilic compound in an amount of about 12% by weight. In one embodiment, the sustained release delivery system includes the hydrophilic compound in an amount of about 8% by weight. In one embodiment, the sustained release delivery system includes the hydrophilic compound in an amount of about 20% by weight. In one embodiment, the sustained release delivery system includes the hydrophilic compound in an amount of about 28% by weight.

The hydrophilic compound is any compound known in the art to be hydrophilic. Exemplary hydrophilic compounds include without limitation gums, cellulose ethers, acrylic resins, polyvinyl pyrrolidone, protein-derived compounds, and mixtures thereof. Exemplary gums include without limitation heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include without limitation hydroxyalkyl celluloses and carboxyalkyl celluloses. In some embodiments, cellulose ethers include hydroxyethyl celluloses, hydroxypropyl celluloses, hydroxypropylmethyl-celluloses, carboxy methylcelluloses, and mixtures thereof. Exemplary acrylic resins include without limitation polymers and copolymers of acrylic acid, methacrylic acid, methyl acrylate and methyl methacrylate. In some embodiments, the hydrophilic compound is a gum. In other embodiments, the hydrophilic compound is a heteropolysaccharide gum. In further embodiments, the hydrophilic compound is a xanthan gum or derivative thereof. Derivatives of xanthan gum include without limitation, for example, deacylated xanthan gum, the carboxymethyl esters of xanthan gum, and the propylene glycol esters of xanthan gum.

In another aspect, the sustained release delivery system further includes at least one cross-linking agent. In one embodiment, the cross-linking agent is a compound that is capable of cross-linking the hydrophilic compound to form a gel matrix in the presence of liquids. As used herein, "liquids" includes, for example, gastrointestinal fluids and aqueous solutions, such as those used for in vitro dissolution testing. The sustained release delivery system generally includes the cross-linking agent in an amount of about 0.5% to about 80% by weight. In one embodiment, the sustained release delivery system generally includes the cross linking agent in an amount of about 12% to about 47% by weight. In another embodiment, the sustained release delivery system generally includes the cross-linking agent in an amount of about 20% to about 30% by weight. In one embodiment, the sustained release delivery system generally includes the cross-linking agent in an amount of about 15% to about 25% by weight. In some embodiments, the at least one cross-linking agent is present in the sustained release delivery system in an amount of about 15%, about 16%, about 17%, about 18%, about 19%, about 20%, about 21%, about 22%, about 23%, about 24%, or about 25% by weight. In one embodiment, the sustained release delivery system includes the cross-linking agent in an amount of about 18% by weight. In one embodiment, the sustained release delivery system includes the cross-linking agent in an amount of about 12% by weight. In one embodiment, the sustained release delivery system includes the cross-linking agent in an amount of about 30% by weight. In one embodiment, the sustained release delivery system includes the cross-linking agent in an amount of about 42% by weight.

Exemplary cross-linking agents include homopolysaccharides. Exemplary homopolysaccharides include without limitation galactomannan gums, such as guar gum, hydroxypropyl guar gum, and locust bean gum. In some embodiments, the cross-linking agent is a locust bean gum or a guar gum. In other embodiments, the cross-linking agent is an alginic acid derivative or hydrocolloid.

In some embodiments, when the sustained release delivery system includes at least one hydrophilic compound and at least one cross-linking agent, the weight ratio of hydrophilic compound to cross-linking agent is from about 1:9 to about 9:1, about 1:8 to about 8:1, about 1:7 to about 7:1, about 1:6 to about 6:1, about 1:5 to about 5:1, about 1:4 to about 4:1, about 1:3 to about 3:1, or about 1:2 to about 2:1. In some embodiments, the weight ratio of hydrophilic compound to cross-linking agent is about 1:5, about 1:4.5, about 1:4, about 1:3.5, about 1:3, about 1:2.5, about 1:2, about 1:1.5, and about 1:1.

When the sustained release delivery system includes at least one hydrophilic compound and at least one cross-linking agent, the weight ratio of the nalbuphine or pharmaceutically acceptable salt thereof to the sum of the at least one hydrophilic compound and the at least one cross-linking agent is from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, or from about 2:1 to about 1:2. In some embodiments, the weight ratio of the nalbuphine or pharmaceutically acceptable salt thereof to the sum of the at least one hydrophilic compound and the at least one cross-linking agent is from about 4:1 to about 1:1, from about 4:1 to about 1:1.5, from about 3:1 to about 1:1, or from about 2:1 to about 1:1. In one embodiment, the ratio of the nalbuphine or pharmaceutically acceptable salt thereof to the sum of the at least one hydrophilic compound and the at least one cross-linking agent is about 5:1, about 4:1 (i.e., 1:0.25), about 3.5:1, about 3:1, about 2.5:1, about 2:1 (i.e., 1:0.5), about 1.9:1, about 1.8:1, about 1.7:1, about 1.6:1, about 1.5:1, about 1.4:1, about 1.3:1, about 1.2:1, about 1.1:1, about 1:1, about 1:1.5, about 1:2, about 1:3, about 1:4, and about 1:5.

The sustained release delivery system further includes one or more pharmaceutical diluents known in the art. Exemplary pharmaceutical diluents include without limitation monosaccharides, disaccharides, polyhydric alcohols and mixtures thereof. In some embodiments, pharmaceutical diluents include, for example, starch, mannitol, lactose, dextrose, sucrose, microcrystalline cellulose, sorbitol, xylitol, fructose, and mixtures thereof. In some embodiments, the pharmaceutical diluent is water-soluble. Nonlimiting examples of water-soluble pharmaceutical diluents include lactose, dextrose, sucrose, or mixtures thereof. The weight ratio of pharmaceutical diluent to hydrophilic compound is generally from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In some embodiments, the weight ratio of pharmaceutical diluent to hydrophilic compound is generally from about 9:1 to about 1:1.5. In some embodiments, the weight ratio of pharmaceutical diluent to hydrophilic compound is about 9:1, about 8.75:1, about 8.5:1, about 8.25:1, about 8:1, about 7.5:1, about 7:1, about 6.5:1, about 6:1, about 5.5:1, about 5:1, about 4.5:1, about 4:1, about 3.5:1, about 3:1, about 2.5:1, about 2:1, about 1.5:1, or about 1:1.

The sustained release delivery system generally includes one or more pharmaceutical diluents in an amount of about 20% to about 80%, about 30% to about 70%, about 40% to about 70%, or about 40% to about 60%. In one embodiment, the sustained release delivery system includes one or more pharmaceutical diluents in an amount of about 20% to about 70% by weight. In one embodiment, the sustained release delivery system includes one or more pharmaceutical diluents in an amount of about 50% to about 85% by weight. In some embodiments, the sustained release delivery system includes one or more pharmaceutical diluents in an amount of about 55%, about 60%, about 65%, about 70%, about 80%, or about 85% by weight. In one embodiment, the sustained release delivery system includes one or more pharmaceutical diluents in an amount of about 20% by weight. In one embodiment, the sustained release delivery system includes one or more pharmaceutical diluents in an amount of about 30% by weight. In one embodiment, the sustained release delivery system includes one or more pharmaceutical diluents in an amount of about 40% by weight. In one embodiment, the sustained release delivery system includes one or more pharmaceutical diluents in an amount of about 50% by weight. In one embodiment, the sustained release delivery system includes one or more pharmaceutical diluents in an amount of about 60% by weight. In one embodiment, the sustained release delivery system includes one or more pharmaceutical diluents in an amount of about 70% by weight.

In a further aspect, the sustained release delivery system of the invention includes one or more cationic cross-linking compounds. In some embodiments, the one or more cationic cross-linking compounds are used instead of the cross-linking agent. In some embodiments, the one or more cationic cross-linking compounds are used in addition to the cross-linking agent. In one embodiment, the one or more cationic cross-linking compounds are used in an amount sufficient to cross-link the hydrophilic compound to form a gel matrix in the presence of liquids. In some embodiments, the one or more cationic cross-linking compounds are present in the sustained release delivery system in an amount of about 0.5% to about 30%, about 0.5% to about 25%, about 0.5% to about 20%, about 0.5% to about 15%, about 0.5% to about 10%, or about 0.5% to about 5% by weight. In some embodiments, the one or more cationic cross-linking compounds are present in the sustained release delivery system in an amount of about 5% to about 20%, about 5% to about 15%, about 6% to about 14%, about 7% to about 13%, about 8% to about 12%, or about 9% to about 11% by weight. In some embodiments, the one or more cationic cross-linking compounds are present in the sustained release delivery system in an amount of about 5%, about 6%, about 7%, about 8%, about 9%, about 10%, about 11%, about 12%, about 13%, about 14%, or about 15% by weight. In one embodiment, the cationic cross-linking compound is present in the sustained release delivery system in an amount of about 10% by weight.

Exemplary cationic cross-linking compounds include without limitation monovalent metal cations, multivalent metal cations, and inorganic salts, including alkali metal and/or alkaline earth metal sulfates, chlorides, borates, bromides, citrates, acetates, lactates, and mixtures thereof. For example, the cationic cross-linking compound include without limitation one or more of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures thereof.

When the sustained release delivery system includes at least one hydrophilic compound and at least one cationic cross-linking compound, the weight ratio of hydrophilic compound to cationic cross-linking compound ranges from about 1:9 to about 9:1, from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In one embodiment, the weight ratio of hydrophilic compound to cationic cross-linking compound ranges from about 1:3 to about 3:1. In some embodiments, the weight ratio of hydrophilic compound to cationic cross-linking compound is about 3:1, about 2.75:1, about 2.5:1, about 2.25:1, about 2:1, about 1.8:1, about 1.6:1, about 1.4:1, about 1.2:1, about 1:1, about 1:1.25, about 1:1.5, or about 1:2. In one embodiment, the weight ratio of hydrophilic compound to cationic cross-linking compound is about 1:1.25. In one embodiment, the weight ratio of hydrophilic compound to cationic cross-linking compound is about 1.2:1. In one embodiment, the weight ratio of hydrophilic compound to cationic cross-linking compound is about 2:1.

In one embodiment, the weight ratio of hydrophilic compound to cationic cross-linking compound is about 2.8:1.

In one embodiment, the at least one hydrophilic compound is present in the sustained release delivery system in an amount of about 5% to about 80% by weight; the at least one cationic cross-linking agent is present in the sustained release delivery system in an amount of about 0.5% to about 30% by weight; and the at least one pharmaceutical diluent is present in the sustained release delivery system in an amount of about 20% to about 80% by weight. In another embodiment, the at least one hydrophilic compound is present in the sustained release delivery system in an amount of about 8% to about 30% by weight; the at least one cationic cross-linking agent is present in the sustained release delivery system in an amount of about 10% by weight; and the at least one pharmaceutical diluent is present in the sustained release delivery system in an amount of about 20% to about 70% by weight. In another embodiment, the at least one hydrophilic compound is present in the sustained release delivery system in an amount of about 5% to about 30% by weight; the at least one cationic cross-linking agent is present in the sustained release delivery system in an amount of about 5% to about 20% by weight; and the at least one pharmaceutical diluent is present in the sustained release delivery system in an amount of about 20% to about 85% by weight. In another embodiment, the at least one hydrophilic compound is present in the sustained release delivery system in an amount of about 10% to about 20% by weight; the at least one cationic cross-linking agent is present in the sustained release delivery system in an amount of about 5% to about 15% by weight; and the at least one pharmaceutical diluent is present in the sustained release delivery system in an amount of about 50% to about 85% by weight. In some embodiments, the at least one hydrophilic compound is present in the sustained release delivery system in an amount of about 8%, about 9%, about 10%, about 11%, about 12%, about 13%, about 14%, about 15%, about 16%, about 17%, about 18%, about 19%, about 20%, about 22%, about 24%, about 26%, about 28%, or about 30% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, about 16%, about 17%, about 18%, about 19%, or about 20%, by weight; and the at least one pharmaceutical diluent is present in the sustained release delivery system in an amount of about 40%, about 45%, about 50%, about 55%, about 60%, about 65%, about 70%, about 80%, or about 85% by weight. In one embodiment, the at least one hydrophilic compound is present in the sustained release delivery system in an amount of about 10%, about 11%, about 12%, about 13%, about 14%, about 15%, about 16%, about 17%, about 18%, about 19%, or about 20% by weight; the at least one cationic cross-linking agent is present in the sustained release delivery system in an amount of about 5%, about 6%, about 7%, about 8%, about 9%, about 10%, about 11%, about 12%, about 13%, about 14%, about 15%, by weight; and the at least one pharmaceutical diluent is present in the sustained release delivery system in an amount of about 55%, about 60%, about 65%, about 70%, about 80%, or about 85% by weight. In one embodiment, the at least one hydrophilic compound is present in the sustained release delivery system in an amount of about 8%, about 12%, or about 20% by weight; the at least one cationic cross-linking agent is present in the sustained release delivery system in an amount of about 10%, about 12%, or about 14% by weight; and the at least one pharmaceutical diluent is present in the sustained release delivery system in an amount of about 40%, about 60%, or about 70% by weight.

In one embodiment, the sustained release delivery system includes about 0.5% to about 80% locust bean gum, about 5% to about 80% xanthan gum, about 20% to about 80% mannitol and about 0.5% to 80% calcium sulfate dihydrate. In one embodiment, the sustained release delivery system includes about 12% to about 47% locust bean gum, about 8% to about 31% xanthan gum, about 20% to about 78% mannitol and about 0.5% to 25% calcium sulfate dihydrate. In one embodiment, the sustained release delivery system includes about 15% to about 25% locust bean gum, about 10% to about 20% xanthan gum, about 50% to about 85% mannitol and about 5% to 15% calcium sulfate dihydrate. In one embodiment, the sustained release delivery system includes about 18% locust bean gum, about 12% xanthan gum, about 60% mannitol and about 10% calcium sulfate dihydrate. In one embodiment, the sustained release delivery system includes about 12% locust bean gum, about 8% xanthan gum, about 70% mannitol and about 10% calcium sulfate dihydrate. In one embodiment, the sustained release delivery system includes about 20% locust bean gum, about 30% xanthan gum, about 40% mannitol and about 10% calcium sulfate dihydrate. In one embodiment, the sustained release delivery system includes about 30% locust bean gum, about 20% xanthan gum, about 40% mannitol and about 10% calcium sulfate dihydrate. In one embodiment, the sustained release delivery system includes about 42% locust bean gum, about 28% xanthan gum, about 20% mannitol and about 10% calcium sulfate dihydrate.

Two properties of the components of this system (e.g., the at least one hydrophilic compound and the at least one cross-linking agent; or the at least one hydrophilic compound and at least one cationic cross-linking compound) that forms a gel matrix upon exposure to liquids are fast hydration of the compounds/agents and the ability to form a gel matrix having a high gel strength. These two properties, which are needed to achieve a slow release gel matrix, are maximized in the invention by the particular combination of compounds (e.g., the at least one hydrophilic compound and the at least one cross-linking agent; or the at least one hydrophilic compound and the at least one cationic cross-linking compound). For example, hydrophilic compounds (e.g., xanthan gum) have excellent water-wicking properties that provide fast hydration. The combination of hydrophilic compounds with materials that are capable of cross-linking the rigid helical ordered structure of the hydrophilic compound (e.g., cross-linking agents and/or cationic cross-linking compounds) thereby acts synergistically to provide a higher than expected viscosity (i.e., high gel strength) of the gel matrix.

In some embodiments, the compositions described herein are further admixed with one or more wetting agents (e.g., polyethoxylated castor oil, polyethoxylated hydrogenated castor oil, polyethoxylated fatty acid from castor oil, polyethoxylated fatty acid from hydrogenated castor oil) one or more lubricants (e.g., magnesium stearate, sodium stearyl fumarate, and the like), one or more buffering agents, one or more colorants, and/or other conventional ingredients.

In some embodiments the compositions of the present invention may contain additional pharmaceutical excipients. For example, in certain embodiments, fumaric acid may be added to the formulations described herein.

In other embodiments, a non-functional coating, e.g., Opadry®, may be added to the compositions described herein.

In some embodiments, the compositions described herein further include a second hydrophilic compound. In some embodiments, the second hydrophilic compound is a cellulose ether. In some embodiments, the second hydrophilic compound is a hydroxyalkyl cellulose or a carboxyalkyl cellulose. In some embodiments, the second hydrophilic compound is a hydroxyethyl cellulose, a hydroxypropyl cellulose, a hydroxypropylmethyl-cellulose, a carboxy methylcellulose, or a mixture thereof. In some embodiments, the second hydrophilic is an ethyl cellulose or wax (e.g., including without limitation cetyl alcohol, stearyl alcohol, white wax, or carnuba wax). The second hydrophilic compound is present in the formulation in an amount ranging from about 5% to about 45%, about 5% to about 25%, about 10% to about 20%, or 12% to about 18% by weight. In some embodiments, the second hydrophilic compound is present in the formulation in an amount of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, or about 45%.

In some embodiments, the weight ratio of the second hydrophilic compound to the nalbuphine or pharmaceutically acceptable salt ranges from about 5:1 to about 1:5, about 4:1 to about 1:4, about 3:1 to about 1:3, about 2:1 to about 1:2, about 1:1 to about 1:3, or about 1:1 to about 1:2. In some embodiments, the weight ratio of the second hydrophilic compound to the nalbuphine or pharmaceutically acceptable salt is about 5:1, about 4:1, about 3:1, about 2:1, about 1:1, about 1:2, about 1:3, about 1:4, or about 1:5.

In some embodiments, the weight ratio of the second hydrophilic compound to the sustained release delivery system ranges from about 10:1 to about 1:10, about 8:1 to about 1:8, about 6:1 to about 1:6, about 4:1 to about 1:4, about 2:1 to about 1:3, about 1:1 to about 1:10, about 1:1 to about 1:6, or about 1:2 to about 1:6. In some embodiments, the weight ratio of the second hydrophilic compound to the sustained release delivery system is about 10:1, about 8:1, about 6:1, about 4:1, about 2:1, about 1:1, about 1:1.5, about 1:2, about 1:2.5, about 1:3, about 1:4, about 1:5, about 1:6, about 1:7, about 1:8, about 1:9 or about 1:10.

In some embodiments, the invention provides oral sustained release solid dosage formulations including from about 1 mg to 200 mg nalbuphine hydrochloride and about 10 mg to about 420 mg of a sustained release delivery system. In these embodiments, the sustained release delivery system includes about 12% to about 42% locust bean gum; about 8.0% to about 28% xanthan gum; about 20% to about 70% mannitol; and about 5% to about 20% calcium sulfate dihydrate. In some embodiments, the invention provides oral sustained release solid dosage formulations including from about 5 mg to about 80 mg nalbuphine hydrochloride and about 80 mg to about 360 mg of a sustained release delivery system. In some embodiments, the invention provides oral sustained release solid dosage formulations including from about 50 mg to about 150 mg nalbuphine hydrochloride and about 100 mg to about 300 mg of a sustained release delivery system.

In some embodiments, the invention provides oral sustained release solid dosage formulations including about 60 mg nalbuphine hydrochloride and from about 25 mg to about 225 mg of a sustained release delivery system. In these embodiments, the sustained release delivery system includes about 18% locust bean gum; about 12% xanthan gum; about 60% mannitol; and about 10% calcium sulfate dihydrate. In some embodiments, the invention provides oral sustained release solid dosage formulations including from about 5 mg to about 80 mg nalbuphine hydrochloride and about 80 mg to about 360 mg of a sustained release delivery system.

In some embodiments, the invention provides oral sustained release solid dosage formulations including about 45 to about 60 mg nalbuphine hydrochloride and from about 100 mg to about 200 mg of a sustained release delivery system. In these embodiments, the sustained release delivery system includes about 15% to about 25% locust bean gum; about 10% to about 20% xanthan gum; about 50% to about 85% mannitol; and about 5% to about 15% calcium sulfate dihydrate.

The sustained release formulations of nalbuphine are orally administrable solid dosage formulations. Nonlimiting examples of oral solid dosage formulations include tablets, capsules including a plurality of granules, sublingual tablets, powders, granules, syrups, and buccal dosage forms. In some embodiments, tablets have an enteric coating or a hydrophilic coating.

The sustained release delivery system is prepared by dry granulation or wet granulation, before the nalbuphine or pharmaceutically acceptable salt thereof is added, although the components may be held together by an agglomeration technique to produce an acceptable product. In the wet granulation technique, the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules of the sustained release delivery system. Thereafter, the sustained release delivery system is mixed in the desired amounts with the nalbuphine or the pharmaceutically acceptable salt thereof and, optionally, one or more wetting agents, one or more lubricants, one or more buffering agents, one or more coloring agents, one or more second hydrophilic compounds, or other conventional ingredients, to produce a granulated composition. The sustained release delivery system and the nalbuphine may be blended with, for example, a high shear mixer. The nalbuphine is preferably finely and homogeneously dispersed in the sustained release delivery system. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

In some embodiments, the nalbuphine formulation is prepared by dry granulation or wet granulation. The components of the sustained release delivery system are added, along with the nalbuphine or pharmaceutically acceptable salt thereof. Alternatively, all of the components may be held together by an agglomeration technique to produce an acceptable product. In the wet granulation technique, nalbuphine or pharmaceutically salt thereof and the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass that is subsequently dried. The dried mass is then milled with conventional equipment into granules. Optionally, one or more wetting agents, one or more lubricants, one or more buffering agents, one or more coloring agents, one or more second hydrophilic compounds, or other conventional ingredients, are also added to the granulation. The granulated composition, in an amount sufficient to make a uniform batch of tablets, is subjected to tableting in a conventional production scale tableting machine at typical compression pressures, i.e., about 2,000-16,000 psi. In some embodiments, the mixture should not be compressed to a point where there is subsequent difficulty with hydration upon exposure to liquids.

The average particle size of the granulated composition is from about 50 μm to about 400 μm by weight. In some embodiments, the average particle size by weight is from about 185 μm to about 265 μm. The average density of the granulated composition is from about 0.3 g/mL to about 0.8 g/mL. In some embodiments, the average density is from about 0.5 g/mL to about 0.7 g/mL. The tablets formed from the granulations are generally from about 4 Kp to about 22 Kp hardness. The average flow of the granulations is from about 25 to about 40 g/sec.

In one aspect, the invention provides a multilayer solid dosage form, in which the layers are formulated to release the nalbuphine hydrochloride at different rates. For example, in one embodiment, the second layer is an extended release layer that includes nalbuphine or a pharmaceutically acceptable salt thereof and a sustained release delivery system designed to release the nalbuphine or the pharmaceutically acceptable salt thereof at a controlled rate so that therapeutically beneficial blood levels are maintained over an extended period of time (e.g., from about 8 to about 12 hours). The first layer is an immediate release layer that includes a formulation of nalbuphine or a pharmaceutically acceptable salt thereof designed to release the nalbuphine or the pharmaceutically acceptable salt thereof at a rate that is faster than the rate of the second layer to achieve a therapeutically beneficial blood level in an immediate period of time (e.g., from about 1 to about 2 hours). In some embodiments, the first layer includes a sustained release delivery system. In some embodiments, the first layer does not include a sustained release delivery system.

In some embodiments, the weight ratio of the second layer to the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In one embodiment, the weight ratio of the second layer to the first layer is about 5:1 to about 1:5. In a further embodiment, the weight ratio of the second layer to the first layer is about 1:1 to about 1:2. In some embodiments, the weight ratio of the second layer to the first layer is about 1:1, about 1:1.2, about 1:1.4, about 1:1.6, about 1:1.8, or about 1:2. In one embodiment, the weight ratio of the second layer to the first layer is about 1:2. In one embodiment, the weight ratio of the second layer to the first layer is about 1:1.4. In some embodiments, the weight ratio of the second layer to the first layer is about 3:1, about 2.5:1, about 2:1, about 1.5:1. In one embodiment, the weight ratio of the second layer to the first layer is about 2.5:1.

The sustained release delivery system of the multilayer dosage form includes (i) at least one hydrophilic compound, at least one cross-linking agent, and at least one pharmaceutical diluent; (ii) at least one hydrophilic compound, at least one cross-linking agent, at least one pharmaceutical diluent, and at least one cationic cross-linking agent different from the first cross-linking agent; or (iii) at least one hydrophilic compound, at least one cationic cross-linking compound, and at least one pharmaceutical diluent. In some embodiments, when the first layer includes a sustained release delivery system, the sustained release delivery system of the first layer includes the same components as the sustained release delivery system of the second layer (e.g., both the first and second layers are one of embodiments (i)-(iii), listed above). In other embodiments, the sustained release delivery system of the first layer includes different components as the sustained release delivery system of the second layer (e.g., the first layer is embodiment (i), listed above, while the second layer is embodiment (iii), listed above). It is recognized that the sustained release delivery system of either layer can be one of embodiments (i)-(iii) listed above. Moreover, it is recognized that in some embodiments, the first layer does not include a sustained release delivery system.

The sustained release delivery system is generally present in the second layer (i.e., extended release layer) in an amount ranging from about 10 mg to about 420 mg. In some embodiments, the sustained release delivery system is present in the second layer in an amount ranging from about 110 mg to about 200 mg. In some embodiments, the sustained release delivery system is present in the second layer in an amount ranging from about 110 mg to about 150 mg. In some embodiments, the sustained release delivery system is present in the second layer in an amount ranging from about 90 mg to about 150 mg. In some embodiments, the sustained release delivery system is present in the second layer in an amount of about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg. In one embodiment, the sustained release delivery system is present in the second layer in an amount of about 123 mg. In one embodiment, the sustained release delivery system is present in the second layer in an amount of about 101 mg. In one embodiment, the sustained release delivery system is present in the second layer in an amount of about 92 mg. In another embodiment, the sustained release delivery system is present in the second layer in an amount of about 112.5 mg. In one embodiment, the sustained release delivery system is present in the second layer in an amount of about 135 mg. In one embodiment, the sustained release delivery system is present in the second layer in an amount of about 150 mg.

Nalbuphine or a pharmaceutically acceptable salt thereof is generally present in the second layer in an amount ranging from about 30 mg to about 60 mg. In some embodiments, nalbuphine or a pharmaceutically acceptable salt thereof is present in the second layer in an amount ranging from about 45 mg to about 60 mg. In one embodiment, nalbuphine or a pharmaceutically acceptable salt thereof is present in the second layer in an amount of about 45 mg. In one embodiment, nalbuphine or a pharmaceutically acceptable salt thereof is present in the second layer in an amount of about 60 mg.

In some embodiments, the weight ratio of nalbuphine or pharmaceutically acceptable salt thereof to the sustained release delivery system in the second layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, or about 2:1 to about 1:2. In one embodiment, the weight ratio of nalbuphine or pharmaceutically acceptable salt thereof to the sustained release delivery system in the second layer is about 1:2 to about 1:4. In one embodiment, the weight ratio of nalbuphine or pharmaceutically acceptable salt thereof to the sustained release delivery system in the second layer is about 1:1 to about 1:5. In some embodiments, the weight ratio of nalbuphine or pharmaceutically acceptable salt thereof to the sustained release delivery system in the second layer is about 1:1, about 1:1.2, about 1:1.4, about 1:1.6, about 1:1.8, about 1:2, about 1:2.5, about 1:3, or about 1:3.5. In one embodiment, the weight ratio of nalbuphine or pharmaceutically acceptable salt thereof to the sustained release delivery system in the second layer is about 1:2.5. In another embodiment, the weight ratio of nalbuphine or pharmaceutically acceptable salt thereof to the sustained release delivery system in the second layer is about 1:3.3. In a further embodiment, the weight ratio of nalbuphine or pharmaceutically acceptable salt thereof to the sustained release delivery system in the second layer is about 1:3. In yet another embodiment, the ratio of nalbuphine or pharmaceutically acceptable salt thereof to the sustained release delivery system in the second layer is about 1:2.

When the sustained release delivery system is present in the first layer (i.e., immediate release layer), it is generally present in an amount ranging from about 0 mg to about 50 mg. In some embodiments, the sustained release delivery system is present in the first layer in an amount ranging from about 5 mg to about 25 mg or from about 5 mg to about 15 mg. In one embodiment, the sustained release delivery system is present in the first layer in an amount of about 3 mg to about 9 mg. In one embodiment, the sustained release delivery system is present in the first layer in an amount of about 4 mg to about 6 mg. In some embodiments, the sustained release delivery system is present in the first layer in an amount of about 2 mg about 4 mg, about 6 mg, about 8 mg, about 10 mg, about 12 mg, about 14 mg, about 15 mg, about 16 mg, about 18 mg, about 20 mg about 25 mg, about 30 mg, about 35 mg, about 40 mg, about 45 mg or about 50 mg. In one embodiment, the sustained release delivery system is present in the first layer in an amount of about 6 mg.

Nalbuphine or a pharmaceutically acceptable salt thereof is generally present in the first layer (i.e., immediate release layer) in an amount ranging from about 5 mg to about 50 mg. In some embodiments, nalbuphine or a pharmaceutically acceptable salt thereof is present in the first layer in an amount ranging from about 5 mg to about 25 mg or from about 10 mg to about 20 mg. In some embodiments, the nalbuphine or a pharmaceutically acceptable salt thereof is present in the first layer in an amount of about 5 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg or about 50 mg. In one embodiment, nalbuphine or a pharmaceutically acceptable salt thereof is present in the first layer in an amount of about 15 mg.

In some embodiments, when the first layer includes a sustained release delivery system, the ratio of nalbuphine or pharmaceutically acceptable salt thereof to the sustained release delivery system in the first layer is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to about 1:3, about 2:1 to about 1:2. In one embodiment, the ratio of nalbuphine or pharmaceutically acceptable salt thereof to the sustained release delivery system in the first layer is about 2:1 to about 4:1. In some embodiments, the ratio of nalbuphine or pharmaceutically acceptable salt thereof to the sustained release delivery system in the first layer is about 5:1, about 4.5:1, about 4:1, about 3.5:1, about 3:1, about 2.5:1, about 2:1, about 1.5:1, or about 1:1. In one embodiment, the ratio of nalbuphine or pharmaceutically acceptable salt thereof to the sustained release delivery system in the first layer is about 2.5:1. In another embodiment, the ratio of nalbuphine or pharmaceutically acceptable salt thereof to the sustained release delivery system in the first layer is about 3:1.

In some embodiments, the multilayer dosage form further includes a pharmaceutical disintegrant. The disintegrant promotes the dissolution and absorption of nalbuphine or pharmaceutically acceptable salt thereof from the immediate release layer. Nonlimiting examples of pharmaceutical disintegrants include croscarmellose sodium, starch glycolate, crospovidone, and unmodified starch. In one embodiment, the disintegrant is in the first layer (i.e., the immediate release layer), of the dosage form. The disintegrant is generally present in the layer in an amount of about 1.5 mg to about 4.5 mg. In one embodiment, the disintegrant is present in an amount of about 3 mg. In one embodiment, the disintegrant is present in the layer in an amount of about 2-10% by weight. In one embodiment, the disintegrant is present in the layer in an amount of about 5% by weight. When the layer contains a sustained release delivery system, the weight ratio of the sustained release delivery system to the disintegrant is in a range of about 5:1 to about 1:5. In some embodiments, the ratio of the sustained release delivery system to the disintegrant is in a range of about 1:1 to about 3:1. In other embodiments, the ratio of the sustained release delivery system to the disintegrant is in a range of about 2:1.

In some embodiments, the multilayer tablets of the invention are prepared by first preparing the immediate release layer and extended release layer blends separately. The extended release layer is prepared as described above. The wet granulation of the extended release layer is then dried and milled to an appropriate size. Magnesium stearate is added and mixed with the milled granulation. The immediate release layer of the invention is prepared by first mixing the nalbuphine or the pharmaceutically acceptable salt thereof with one or more diluents (e.g., microcrystalline cellulose). This mix is then optionally mixed with one or more disintegrants. The blend is mixed with magnesium stearate. Finally, the immediate release layer blend and the extended release layer blend are compressed into multi-layer (e.g., bi-layer) tablets.

The invention provides methods for treating pain by administering an effective amount of a sustained release formulation of nalbuphine to a patient in need thereof. An effective amount is an amount sufficient to eliminate all pain or to alleviate the pain (i.e., reduce the pain compared to the pain present prior to administration of the nalbuphine sustained release formulation). "Sustained release" or "extended release" means that the nalbuphine or pharmaceutically acceptable salt thereof is released from the formulation at a controlled rate so that therapeutically beneficial blood levels (but below toxic levels) of the nalbuphine or pharmaceutically acceptable salt thereof are maintained over an extended period of time. Alternatively, "sustained release" or "extended release" means that the desired pharmacologic effect is maintained over an extended period of time. Clinical trials of the formulations described herein have surprisingly found that the duration of analgesic effect is longer than expected. The half-life of experimental orally administered nalbuphine formulations (i.e., immediate release formulations) has been reported to be relatively short, only about 5-7 hours. Moreover, the published literature suggests that the duration of effect for experimental formulations of immediate release nalbuphine was only about 4 hours. Based on these data, it was expected that a sustained release formulation would provide a duration of analgesic effect for approximately 6-8 hours, i.e., allowing for 2-3 times daily dosing. In the clinical trials described herein, however, it was surprisingly discovered that the nalbuphine sustained release formulations had an analgesic effect of longer than 8 hours. In some cases, the duration of analgesic effect was at least about 12 hours, thus providing the possibility of fewer dosing administrations, which was heretofore not thought to be possible.

Without wishing to be bound by a particular theory, the longer than expected duration of analgesic effect is thought to be due to the enterohepatic recirculation of nalbuphine. Nalbuphine forms a glucuronic acid or other type of conjugated metabolite in vivo through enzymatic reaction with an enzyme system such as UDP-glucuronyl transferase. It is also possible that enterohepatic recirculation also occurs when parent drug in the bile is released from the gallbladder into the intestine and reabsorbed. Once formed, the conjugated nalbuphine product is thought to be transported into the gastrointestinal tract via biliary secretion whereby the drug conjugate is cleaved liberating nalbuphine which can be reabsorbed from the intestine. It is thought that nalbuphine formulations that have been tested in the past that had a large bolus of nalbuphine in an immediate release formulation (e.g., greater than about 25 mg) may have saturated the enzymatic conjugation system, allowing other digestive or hepatic enzymes (e.g., the cytochrome P450 enzymes) to metabolize the nalbuphine into non-therapeutically active metabolites of nalbuphine and resulting in low oral availability for nalbuphine itself. The sustained release formulation may improve bioavailability and, thus the duration of analgesic effect, by more slowly releasing nalbuphine into the in vivo system and allowing more drug to be conjugated and therefore available for recirculation and later reabsorption from the intestine.

The sustained release formulations of nalbuphine are administered in an amount sufficient to alleviate pain for a period ranging from about 6 hours to about 18 hours. In some embodiments, the formulations are administered in an amount sufficient to alleviate pain up to about 6 hours to about 8 hours. In other embodiments, the formulations are administered in an amount sufficient to alleviate pain up to about 8 hours to about 12 hours. In some embodiments, the formulations are administered in an amount sufficient to alleviate pain up to about 12 hours. In some embodiments, the formulations are administered in an amount sufficient to alleviate pain for at least about 12 hours, 15 hours, or 18 hours. The nalbuphine sustained release oral solid dosage formulations of the invention are administered one to four times a day. In some embodiments, the formulations are administered one to three times a day. In some embodiments, the formulations are administered three times a day. In other embodiments, the formulations are administered two times a day. In still other embodiments, the formulations are administered one time a day. In some embodiments, the pain is minor to moderate to severe. In other embodiments, the pain is moderate to severe. In some embodiments, the nalbuphine formulations disclosed herein are appropriate for treating a patient experiencing chronic pain (i.e., where pain is experienced over a long term, such as lasting months, years or life-long). Exemplary conditions that the pain is associated with include without limitation back pain (e.g., low-back pain), cancer, autoimmune diseases, infections, surgical traumas, accidental traumas or osteoarthritis. In some embodiments, the nalbuphine formulations disclosed herein are useful for treating nociceptive pain (e.g., chronic lower back pain, pain associated with cancer, HIV infection, rheumatoid arthritis, osteoarthritis, trauma (e.g., sprains, bone fractures, burns, bumps, bruises), inflammation, myofascial pain, or post-operative pain), neuropathic pain (e.g., pain associated with diabetic neuropathy, postherpetic neuralgia, CLBT, cancer, HIV infection or AIDS, nerve injury, the "dynias" (e.g., vulvodynia), phantom limb pain, root avulsions, painful traumatic mononeuropathy, painful polyneuropathy, trigeminal neuralgia, post-stroke pain, multiple sclerosis-associated pain, spinal cord injury, neuropathies-associated pain such as in idiopathic or post-traumatic neuropathy and mononeuritis, carpal tunnel-associated neuropathic pain, spinal cord injury-associated pain, complex regional pain syndrome, fibromyalgia-associated neuropathic pain, lumbar and cervical pain, reflex sympathic dystrophy, and neuropathic pain associated with drug therapy), visceral pain (e.g., pain caused, for example, by a burn, a bruise, an abrasion, a laceration, a broken bone, a torn ligament, a torn tendon, a torn muscle, a viral infection, a bacterial infection, a protozoal infection, a fungal infection, contact dermatitis, inflammation, or cancer), and idiopathic pain (e.g., pain associated with fibromyalgia and regional myofascial pain syndromes, arthritis, chronic fatigue syndrome, irritable bowel syndrome, interstitial cystitis, and carpal tunnel syndrome) and other chronic and debilitating condition-associated pain syndromes. In some embodiments, the patient is an animal. In other embodiments, the patient is a mammal. In further embodiments, the patient is a human.

In one aspect, the uses of the sustained release formulations of nalbuphine further include the use of one or more therapeutic agents selected from the group consisting of opioids, non-opioid analgesics, non-steroidal anti-inflammatory drugs (NSAIDs), COX-2 inhibitors, acetaminophen, diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, rofecoxib, valdecoxib, codeine, morphine, methadone, oxymorphone, hydromorphone, oxycodone, hydrocodone, levorphanol, fentanyl, meperidine, timerol, tramadol, naloxone, Stadol, Talwin, buprenorphine, butorphanol, naltrexone and aspirin.

In certain embodiments, the chemistry of certain of the components of the formulation, such as the hydrophilic compound (e.g., xanthan gum), is such that the components are considered to be self-buffering agents which are substantially insensitive to the solubility of the nalbuphine and the pH changes along the length of the gastrointestinal tract. Moreover, the chemistry of the components is believed to be similar to certain known muco-adhesive substances, such as polycarbophil. Muco-adhesive properties are desirable for buccal delivery systems. Thus, the sustained release formulation can loosely interact with the mucin in the gastrointestinal tract and thereby provide another mode by which a constant rate of delivery of the nalbuphine is achieved.

The two phenomenon discussed above (buoyancy and muco-adhesive properties) are mechanisms by which the sustained release formulations of the invention can interact with the mucin and fluids of the gastrointestinal tract and provide a constant rate of delivery of the nalbuphine.

When measured by USP Procedure Drug Release General Chapter <711> Dissolution, (incorporated by reference herein in its entirety), the sustained release formulations of the invention generally exhibit an in vitro dissolution of about 15% to about 50% by weight nalbuphine after 1 hour, about 45% to about 80% by weight nalbuphine after 4 hours, or at least about 80% by weight nalbuphine after 10 hours. In some embodiments, the in vitro and in vivo release characteristics of the sustained release formulations of the invention are modified using mixtures of one or more different water insoluble and/or water soluble compounds, using different plasticizers, varying the thickness of the sustained release film, including providing release-modifying compounds in the coating, and/or by providing passageways through the coating. In some embodiments, the dissolution rate is determined using apparatus USP Type III/250 mL at pH 6.8, 37° C. and 15 dpm. In some embodiments, the dissolution rate is determined using apparatus USP Type III/250 mL performed in pH change (0-1 hours pH 1.2, after hour 1 pH 4.5, after hour 2 pH 6.8) at 37° C. and 15 dpm.

In some embodiments, the sustained release formulation has an in vitro dissolution of about 50% to about 100% by weight nalbuphine after about 6 hours. In some embodiments, the sustained release formulation has an in vitro dissolution of about 75% to about 100% by weight nalbuphine after about 6 hours. In other embodiments, the sustained release formulation has an in vitro dissolution of about 75% to about 100% by weight nalbuphine from about 6 hours to about 8 hours. In further embodiments, the sustained release formulation has an in vitro dissolution of about 80% to about 100% by weight nalbuphine after about 12 hours. In still other embodiments, the sustained release formulation has an in vitro dissolution of about 80% to about 100% by weight nalbuphine from about 12 hours to about 24 hours. In some embodiments, the sustained release formulation has an in vitro dissolution of about 80% to about 100% after about 8 hours to about 12 hours. In yet other embodiments, the sustained release formulation has an in vitro dissolution of about 15% to about 75% by weight nalbuphine after about 1 hour. In still further embodiments, the sustained release formulation has an in vitro dissolution of about 50% by weight nalbuphine after about 1 hour. In some embodiments, the sustained release formulation has an in vitro dissolution of about 50% by weight nalbuphine after about 1 hour and about 75% to about 100% by weight nalbuphine from about 6 hours to about 8 hours. In some embodiments, the sustained release formulation has an in vitro dissolution of about 50% by weight nalbuphine after about 1 hour and about 75% to about 100% by weight nalbuphine from about 8 hours to about 12 hours. In some embodiments, the sustained release formulation has an in vitro dissolution of about 50% by weight nalbuphine after about 1 hour and about 75% to about 100% by weight nalbuphine from about 12 hours to about 24 hours. In some embodiments, the sustained release formulation has an in vitro dissolution of about 50% by weight nalbuphine after about 1 hour and about 80% to about 100% by weight nalbuphine after about 12 hours.

Where the tablet is a multilayer dosage form having a first extended release layer and a second, immediate release, layer, the sustained release formulation has an in vitro dissolution of about 25% to about 75% by weight nalbuphine after about 1 hour. In some embodiments, the multilayer dosage form has an in vitro dissolution of about 25% by weight nalbuphine after about 1 hour. In some embodiments, the multilayer dosage form has an in vitro dissolution of about 50% by weight nalbuphine after about 1 hour. In some embodiments, the multilayer dosage form has an in vitro dissolution of about 75% to about 100% nalbuphine after about 6-8 hours. In some embodiments, the multilayer dosage form has an in vitro dissolution of about 75% to about 100% nalbuphine after about 8-12 hours. In some embodiments, the multilayer dosage form has an in vitro dissolution of about 75% to about 100% nalbuphine after about 12-24 hours. In some embodiments, the multilayer dosage form has an in vitro dissolution of about 75% to about 100% nalbuphine after about 12 hours.

When administered orally to patients the sustained release formulations described herein exhibit the following in vivo characteristics: (a) a peak plasma level of nalbuphine occurs within about 2 to about 6 hours after administration; (b) onset of nalbuphine analgesic effect from about 30 minutes of dosing to within about 6 hours of dosing; (c) duration of the nalbuphine analgesic effect is about 2 to about 24 hours; and (d) the relative nalbuphine bioavailability is about 0.5 to about 1.5 compared to an orally administered aqueous solution of nalbuphine. The time of onset for an analgesic effect can depend on at least on dosing and the type of pain relief sought. In some embodiments, the duration of the nalbuphine analgesic effect is at least about 8 hours. In some embodiments, the duration of the nalbuphine analgesic effect is at least about 9 hours. In some embodiments, the duration of the nalbuphine analgesic effect is at least about 10 hours. In some embodiments, the duration of the nalbuphine analgesic effect is at least about 1 hours. In some embodiments, the duration of the nalbuphine analgesic effect is at least about 12 hours. In some embodiments, the duration of nalbuphine analgesic effect is about 6, hours, 8 hours, 10 hours, 12 hours, 15 hours, or 18 hours. In some embodiments, the relative nalbuphine bioavailability is about 1.25 compared to an orally administered aqueous solution of nalbuphine. In some embodiments, the relative nalbuphine bioavailability is about 1.35 compared to an orally administered aqueous solution of nalbuphine.

In some embodiments, the sustained release nalbuphine formulations described herein invention provides an oral unit dosage form including nalbuphine or a pharmaceutically acceptable salt thereof. The oral dosage form provides an analgesic effect over a period of at least about 6 hours, about 7 hours, about 8 hours, about 9 hours, about 10 hours, about 11 hours, about 12 hours, about 13 hours, about 14 hours, about 15 hours, about 16 hours, about 17 hours, or about 18 hours. In some embodiments, the oral dosage form provides an analgesic effect over a period of about 6-18 hours, about 8-16 hours, about 8-12 hours, or about 8-10 hours. The oral dosage form provides an analgesic effect over a period of about 6 hours, about 7 hours, about 8 hours, about 9 hours, about 10 hours, about 11 hours, about 12 hours, about 13 hours, about 14 hours, about 15 hours, about 16 hours, about 17 hours, or about 18 hours.

In some embodiments, the oral dosage form provides a blood serum level of nalbuphine characterized by one or more peaks followed by a plateau region. The plateau region is characterized as having a relatively consistent blood serum level of nalbuphine (e.g., the blood serum level of nalbuphine does not consistently increase or decrease from time point to time point). In some embodiments, the plateau region is characterized as having a consistent average blood serum level of nalbuphine. The plateau region is contrasted with the region following the plateau region, in which the blood serum level of nalbuphine generally decreases from one time point to the next. In some embodiments, the plateau region has a duration of at least about 1 hour, about 2 hours, about 3 hours, about 4 hours, about 5 hours, about 6 hours, about 7 hours, about 8 hours, about 9 hours, about 10 hours, about 11 hours or about 12 hours. In some embodiments, the plateau region has a duration from about 1 hour to about 12 hours, from about 2 hours to about 10 hours, from about 2 hours to about 8 hours, from about 2 hours to about 7 hours or from about 4 hours to about 10 hours, from about 4 hours to about 8 hours, or from about 4 hours to about 6 hours. In some embodiments, the blood serum level of nalbuphine at each time point in the plateau region ranges from about 75% to about 125% of the mean blood serum level in the plateau region. In some embodiments, the blood serum level of nalbuphine at each time point in the plateau region ranges from about 80% to about 120% of the mean blood serum level in the plateau region. In some embodiments, the blood serum level of nalbuphine at each time point in the plateau region ranges from about 85% to about 115% of the mean blood serum level in the plateau region. In some embodiments, the blood serum level of nalbuphine at each time point in the plateau region ranges from about 90% to about 110% of the mean blood serum level in the plateau region. In some embodiments, the minimum blood serum level of nalbuphine observed during the plateau region is not more than about 25% below the mean blood serum level for all time points in the plateau region. In some embodiments, the minimum blood serum level of nalbuphine observed during the plateau region is not more than about 20% below the mean blood serum level in the plateau region. In some embodiments, the minimum blood serum level of nalbuphine observed during the plateau region is not more than about 15% below the mean blood serum level in the plateau region. In some embodiments, the minimum blood serum level of nalbuphine observed during the plateau region ranges from about 75% to about 100% of the mean blood serum level in the plateau region. In some embodiments, the minimum blood serum level of nalbuphine observed during the plateau region ranges from about 80% to about 100% of the mean blood serum level in the plateau region. In some embodiments, the minimum blood serum level of nalbuphine observed during the plateau region ranges from about 85% to about 100% of the mean blood serum level in the plateau region. In some embodiments, the minimum blood serum level of nalbuphine observed during the plateau region ranges from about 80% to about 95% of the mean blood serum level in the plateau region.

While the compositions of the invention may be administered as the sole active pharmaceutical compound in the methods described herein, they can also be used in combination with one or more compounds which are known to be therapeutically effective against pain.

The invention further provides methods of treating pain comprising administering to a mammal in need thereof the sustained release nalbuphine formulations described herein in an amount effective to treat pain. In some embodiments, methods of treating pain include treating chronic pain or acute pain. In some embodiments, methods of treating pain include nociceptive pain, europathis pain, visceral pain or idiopathic pain.

The sustained release nalbuphine formulations described herein are also useful in the manufacture of medicaments for treating pain in a mammal. In some embodiments, the formulations are useful in the manufacture of medicaments for treating pain in a mammal.

The invention also provides pharmaceutical kits including one or more containers filled with one or more of the compositions of the invention. The kits may further include other pharmaceutical compounds known in the art to be therapeutically effective against pain, and instructions for use, in particular instructions for using the compositions for the treatment of pain, including chronic pain. In one embodiment, the invention provides a package or a kit including the sustained release compositions described herein and instructions for treating pain.

DETAILED DESCRIPTION OF THE PREFERRED EMBODIMENTS

EXAMPLES

The following examples are for purposes of illustration only and are not intended to limit the scope of the appended claims.

Examples 1 to 3

Three sustained release delivery systems were prepared by dry blending xanthan gum, locust bean gum, calcium sulfate dihydrate, and mannitol in a high speed mixed/granulator for 3 minutes. While running choppers/impellers, water was sprayed to the dry blended mixture, and granulated for another 6 minutes. Then the granulation process was stopped and the mixer/granulation bowl was scraped. While running choppers/impellers, the granulation was mixed for one more minute. After the granulation was checked for consistency, while running choppers/impellers additional water was added to the granulation and granulated for additional 3.5 minutes. The granulation was then dried to LOD (loss on drying) of less than about 4% by weight. The granulation was then milled using screen #1521-0033. The relative quantities of the ingredients are listed in Table 1.

TABLE 1

Sustained Release Delivery System

| Excipient | Example 1 % | Example 2 % | Example 3 % |
|---|---|---|---|
| Xanthan Gum, NF | 8.0 | 12.0 | 20.0 |
| Locust Bean Gum, FCC | 12.0 | 18.0 | 30.0 |
| Mannitol, USP | 70.0 | 60.0 | 40.0 |
| Calcium Sulfate Dihydrate, NF | 10.0 | 10.0 | 10.0 |
| Sterile Water for Injection, USP[1] | — | — | — |
| Total | 100.0 | 100.0 | 100.0 |

[1]Sterile Water for Injection, USP is removed during processing

Examples 4 to 7

A series of tablets containing different amounts of gum were prepared using the sustained release delivery system of Example 3. The quantities of ingredients per tablet are listed in Table 2.

TABLE 2

| Component | Ex. 4 mg | Ex. 5 mg | Ex. 6 mg | Ex. 7 mg |
|---|---|---|---|---|
| Nalbuphine HCl, USP | 60 | 60 | 60 | 60 |
| Sustained release deliverly system | 60[1] | 120[1] | 180[1] | 90[1] |
| Magnesium stearate, NF | 0.5 | 1.8 | 1.2 | 0.75 |
| Total Weight | 120.5 | 181.8 | 241.2 | 150.75 |
| Active:Gum | 1:0.5 | 1:1 | 1:1.5 | 1:0.75 |
| Tooling Size | 0.2812" | 0.2812" | 0.3125" | 0.2812" |
| Hardness (Kp) | 1.2 | 8.8 | 8.9 | 7.2 |

[1]Sustained release system of Example 3

The tablets were prepared by mixing nalbuphine with the sustained release delivery system in a mixer. The magnesium stearate was passed through a #30 mesh screen sieve and then mixed with the dry blend containing nalbuphine and the sustained release delivery system. This lubricated blend was compressed using the tooling as specified in Table 2 to make tablets of the total weight indicated.

The tablets of Examples 4-7 were tested for in vitro % release rate according to USP Procedure Drug Release General Chapter <711> Dissolution, using apparatus USP Type III/250 ml. The test was performed at pH 6.8, 37° C./15 dpm (dips per minute) in 100 mM ammonium phosphate buffer. The results are shown in Table 3.

TABLE 3

| Dissolution Time (hours) | Example 4 pH 6.8 | Example 5 pH 6.8 | Example 6 pH 6.8 | Example 7 pH 6.8 |
|---|---|---|---|---|
| 0 | 0 | 0 | 0 | 0 |
| 1 | 29.3 | 23.8 | 19.5 | 25.0 |
| 2 | 41.8 | 35.1 | 29.4 | 35.9 |
| 4 | 59.2 | 51.7 | 45.0 | 53.0 |
| 6 | 72.9 | 65.6 | 56.4 | 67.1 |
| 8 | 84.2 | 77.8 | 65.3 | 79.6 |
| 12 | 98.1 | 92.9 | 81.0 | 93.9 |
| Remnant | 4.3 | 5.9 | 16.3 | 6.0 |
| % Recovery | 102.4 | 98.8 | 97.3 | 99.9 |

Examples 8 to 10

A series of tablets containing different amounts of gum and different sustained release delivery systems were prepared using the sustained release delivery systems of Examples 1 and 2. The quantities of ingredients per tablet are listed in Table 4.

TABLE 4

| Component | Ext. 8 mg | Ex. 9 mg | Ex. 10\ mg |
|---|---|---|---|
| Nalbuphine HCl, USP | 60 | 60 | 60 |
| Sustained release delivery system | 225[2] | 150[3] | 100[3] |
| Magnesium stearate | 1.43 | 1.1 | 0.8 |
| Total weight | 286.4 | 211.1 | 160.8 |
| Active:Gum | 1:0.75 | 1:0.75 | 1:0.5 |
| Tooling Size | 0.3125" | 0.3125" | 0.2812" |
| Hardness (Kp) | 20 | 17 | 20 |

[2]Sustained release delivery system of Example 1
[3]Sustained release delivery system of Example 2

The tablets were prepared by first mixing nalbuphine with the sustained release delivery system in a mixer for Example 8 and in a high shear granulator for Example 9 and 10. For Examples 9 and 10, the blend was then granulated with water until consistent granulation was achieved, followed by drying in a fluidized bed dryer for 30 minutes at 70° C. The dried granules were then passed through a Fitzmill at 2500 rpm using 1521-0050 screen. The magnesium stearate was passed through a #30 mesh screen sieve, and then mixed with the milled granules for Examples 9 and 10 and with the dry blend for Example 8 for 5 minutes. The lubricated blend was compressed using the tooling as specified in Table 4 to make tablets of the total weight indicated.

The tablets of Examples 8-10 were tested for in vitro % release rate according to USP Procedure Drug Release General Chapter <711> Dissolution, using apparatus USP Type III/250 ml. The test was performed in pH change, at 37° C./15 dpm. The pH change was as follows: pH 1.2 for the first hour, pH 4.5 for the second hour, and pH 6.8 after the second hour and through the duration of the test. The results are shown in Table 5.

TABLE 5

| Dissolution Time (hours) | Example 8 pH change | Example 9 pH change | Example 10 pH change |
|---|---|---|---|
| 0 | 0.0 | 0 | 0 |
| 1 | 19.4 | 18.8 | 22.5 |
| 2 | 36.4 | 39.7 | 45.3 |
| 4 | 59.0 | 66.3 | 73.2 |
| 6 | 72.5 | 82.6 | 89 |
| 8 | 79.4 | 89.8 | 95.9 |
| 12 | 82.1 | 92.3 | 100.1 |
| Remnant | 0.1 | 0.1 | 0.8 |
| % Recovery | 82.2 | 92.4 | 100.9 |

Examples 11 to 16

To determine the effect of the amount of gum in combination with microcrystalline cellulose (Emococel 90M), six batches of tablets were prepared using the sustained release delivery system of Example 3. The range of Active:Gum ratios used in Examples 11-16 varied between 1:0.25 and 1:0.5. Compositions of the tablets are shown in Table 6.

TABLE 6

| Ingredient | Ex. 11 mg/tab | Ex. 12 mg/tab | Ex. 13 mg/tab | Ex. 14 mg/tab | Ex. 15 mg/tab | Ex. 16 mg/tab |
|---|---|---|---|---|---|---|
| Sustained release delivery system | 30[4] | 60[4] | 60[4] | 30[4] | 60[4] | 60[4] |
| Nalbuphine HCl | 60 | 60 | 60 | 60 | 60 | 60 |
| Microcrystalline Cellulose | 30 | 30 | 60 | 60 | 120 | — |
| Magnesium stearate | 0.6 | 0.8 | 0.9 | 0.8 | 1.2 | 0.6 |
| Total Weight (mg) | 120.6 | 150.8 | 180.9 | 150.8 | 241.2 | 120.6 |
| Active:Gum | 1:0.25 | 1:0.5 | 1:0.5 | 1:0.25 | 1:0.5 | 1:0.5 |
| Tooling Size | 0.2500" | 0.2812" | 0.2812" | 0.2812" | 0.3125" | 0.2500" |
| Hardness (Kp) | 10.2 | 10 | 12 | 13 | 22 | 13.2 |

Sustained release delivery system of Example 3

The tablets of Examples 11-15 were prepared by first sifting magnesium stearate through #30 mesh screen sieve. Then blend nalbuphine with the sustained release delivery system, and magnesium stearate in a blender for 5 minutes. The lubricated blend was compressed using the tooling as specified in Table 6 to make tablets of the total weight indicated.

The tablets of Example 16 were prepared by mixing nalbuphine in a high shear granulator with the sustained release delivery system. The blend was then granulated with water until consistent granulation was achieved. The granulation is then dried in a fluidized bed dryer for 40 minutes at 70° C. The dried granules were then passed through a Fitzmill at 2500 rpm using 1521-0050 screen. The magnesium stearate was passed through a #30 mesh screen sieve and then mixed with the milled granules for 5 minutes. The lubricated blend was compressed using the tooling as specified in Table 6 to make tablets of the total weight indicated.

The tablets of Examples 11-16 were tested for in vitro % release rate according to USP Procedure Drug Release General Chapter <711> Dissolution, using apparatus USP Type III/250 ml. The test was performed in pH change, at 37° C./15 dpm, as described above for Examples 8-10. The results are shown in Table 7.

TABLE 7

| Dissolution time (hours) | Ex. 11 pH change | Ex. 12 pH change | Ex. 13 pH change | Ex. 14 pH change | Ex. 15 pH change | Ex. 16 pH change |
|---|---|---|---|---|---|---|
| 0 | 0.0 | 0.0 | 0.0 | 0.0 | 0.0 | 0.0 |
| 1 | 93.2 | 59.4 | 94.5 | 93.4 | 92.1 | 17.1 |
| 2 | 94.4 | 73.0 | 96.0 | 94.8 | 93.4 | 39.7 |
| 4 | 94.5 | 84.5 | 96.0 | 94.8 | 93.5 | 64.4 |
| 6 | 94.5 | 87.4 | 96.0 | 94.8 | 93.5 | 74.6 |
| 8 | 94.5 | 88.7 | 96.0 | 94.8 | 93.5 | 81.5 |
| 12 | 94.5 | 90.2 | 96.0 | 94.8 | 93.5 | 93.1 |
| Remnant | 0.0 | 1.2 | 0.0 | 0.0 | 0.0 | 7.0 |
| % Recovery | 94.5 | 91.5 | 96.0 | 94.8 | 93.5 | 100.1 |

Examples 17 and 18

Two batches of bi-layer tablets were prepared using the sustained release delivery system of Example 2 (Examples 17 and 18). In the bi-layer tablets, the first layer of the tablets was formulated to provide relatively a slow sustained release; the second layer was formulated to provide relatively fast (immediate) release. The in vitro dissolution profiles of the bi-layer tablets were compared to the dissolution profile of single layer tablets that were formulated to provide a sustained release (Example 9). Compositions of the tablets are shown in Table 8.

TABLE 8

| Ingredient | Example 17 mg/tab | Example 18 mg/tab | Example 9 mg/tab |
|---|---|---|---|
| Extended release layer (ER) | | | |
| Sustained release delivery system | 112.5[5] | 112.9[5] | 150 |
| Nalbuphine HCl | 45 | 45 | 60 |
| Magnesium stearate | 0.8 | 0.8 | 1.1 |
| ER weight | 158.3 | 158.3 | 211.1 |
| Immediate release layer (IR) | | | |
| Sustained release delivery system | 6.0[5] | | N/A |
| Nalbuphine HCl | 15.0 | | N/A |
| Microcrystalline Cellulose, NF (Emcocel 90 M) | 35.7 | | N/A |
| Croscarmellose Sodium, NF (Primellose ®) | 3.0 | | N/A |
| Magnesium stearate, NF | 0.3 | | N/A |
| IR Weight | 60.0 | | N/A |
| Total Weight | 218.3 | 218.3 | 211.1 |
| Active:Gum | 1:0.6 | 1:0.6 | 1:0.75 |
| Tooling Size | 0.2812" | 0.2812" | 0.3125" |
| Hardness | N/A | N/A | 17 |

[5]Sustained release delivery system of Example 2

For the extended release layer, the nalbuphine was mixed with the sustained release delivery system in a high shear granulator for 3 minutes. The mixture was granulated with water until consistent granulation was achieved, then the wet mass was dried in a fluidized bed dryer for 20 minutes at 70° C. The dried granules were then passed through a Fitzmill at 2500 rpm using 1521-0050 screen. For the immediate release layer, the nalbuphine was blended with the sustained release delivery system, microcrystalline cellulose (Emcocel® 90M), and croscarmellose sodium, NF (Primellose®) in a V-Blender for 10 minutes. The magnesium stearate was passed through a #30 mesh screen sieve. The milled granules of the slow release layer was mixed with the sieved magnesium stearate in a V-blender for 5 minutes and the dry blend of the immediate release layer was mixed with the sieved magnesium stearate in a V-blender for 5 minutes, separately. This lubricated blend of the extended release layer and the immediate release layer were then compressed into bi-layer tablets using the tooling specified in Table 8, to make the tablets of the total weight indicated.

The tablets of Examples 17-18 were tested for in vitro % release rate according to USP Procedure Drug Release USP General Chapter <711> Dissolution, using apparatus USP Type III/250 ml. The test was performed in pH change as described above for Examples 8-10, at 37° C./15 dpm, as described above for Examples 8-10. The results are shown in Table 9. For purposes of comparing the dissolution profiles of the bi-layer tablets with a single-layer tablet, the dissolution data for Example 9 is also shown in Table 9.

TABLE 9

| Dissolution time (hours) | Ex. 17 pH change | Ex. 18 pH change | Ex. 9 pH change |
|---|---|---|---|
| 0 | 0 | 0.0 | 0 |
| 1 | 44.5 | 42.6 | 18.0 |
| 2 | 62.8 | 62.7 | 39.7 |
| 4 | 83.1 | 84.3 | 66.3 |
| 6 | 92.3 | 92.3 | 82.6 |
| 8 | 94.0 | 93.7 | 89.8 |
| 12 | 94.0 | 93.9 | 92.3 |
| Remnant | 0.0 | 0 | 0.1 |
| % Recovery | 94.1 | 93.9 | 92.4 |

Examples 19 and 20

For a clinical study, one batch of bi-layer tablets and one batch of single layer tablets were prepared using the sustained release delivery system of Example 2. The first layer of the tablets was formulated to provide relatively a slow sustained release; the second layer was formulated to provide relatively fast (immediate release). Compositions of the tablets are shown in Table 10.

TABLE 10

| Component | Amount mg/tablet (%) | |
|---|---|---|
| Ingredient | Example 19(F-2) | Example 20(F-1) |
| Extended release player (ER) | | |
| Sustained Release Excipient (30%) | 112.5[6] | 150.0[6] |
| Nalbuphine HCl | 45.0 | 60.0 |
| Magnesium stearate, NF | 0.8 | 1.10 |
| Sterile Water for injection, USP* | * | * |
| Mg/tablet weight (ER portion) | 158.3 | 211.1 |
| Immediate release layer (IR) | | |
| Nalbuphine HCl | 15.0 | |
| Microcrystalline Cellulose, NF | 41.7 | |
| Croscarmellose Sodium, NF | 3.0 | |
| Magnesium stearate, NF | 0.3 | |
| Mg/tablet weight (IR portion) | 60.0 | |
| Total Weight (mg/tablet) | 218.3 | 211.1 |
| Type of tablet | Bi-layer(ER/IR) | Single layer (ER) |
| Active to Gum Ratio | 1:0.75 | 1:0.75 |
| Tooling Size | 0.3125 | 0.3125 |
| Hardness | ~11 Kp | ~11 Kp |

*Sterile Water for Injection, USP is removed during process
[6]Sustained release delivery system of Example 2

For the extended release layer of Example 19 and 20, the nalbuphine was mixed with the sustained release delivery system in a high shear granulator (6-liter Diosna-Pharma Mixer 1/6) for 5 minutes with the impeller speed at 300 rpm and the chopper off. After the mixer stopped, the bowl was scraped and sample was taken for LOD. While the impeller and the chopper are running at 300 rpm, the mixture was granulated with water for 2 minutes. After the mixer stopped, the bowl was scraped. While impeller speed is running at 500 rpm and the chopper speed at 300 rpm, the granulation was continued by mixing for an additional 1 minute. At the end of mixing the bowel was scraped. While the impeller and chopper were running at 300 rpm, additional of water (about 50.0 g) was added and granulated for 2 minutes in Example 19 and for 1 minute in Example 20. To achieve consistent granules, the granulation was mixed for additional 3 minutes in Example 19 and 1 minute in Example 20, while the impeller and chopper were running at 500 and 300 rpm, respectively. Then the wet mass was dried in a Uni-Glatt fluid bed dryer for 30 minutes at 70° C. The dried granules were then passed through a Fitzmill, knives forward, with the speed of 2200-2700 rpm using 1521-0033 screen. The magnesium stearate was passed through a #30 mesh screen sieve. The milled granules of the extended release layer for Example 19 and 20 were mixed separately with the sieved magnesium stearate in a V-blender with a 4-quart stainless steel shell for 5 minutes.

For Example 20, the lubricated blend of the extended release layer was compressed into single layer tablets with the Piccola tablet press using the tooling specified in Table 1, to make the tablets of the total weight indicated.

In the immediate release layer portion of Example 19, the nalbuphine was blended with the microcrystalline cellulose (Emcocel 90M) in a P-K Blend Master V-Blender for 5 minutes. To the mixture, croscarmellose sodium, NF (Primellose®) was added and mixed for 5 minutes. The magnesium stearate was passed through a #30 mesh screen sieve. The milled granules of the extended release layer portion of Example 19 was mixed with the sieved magnesium stearate in a V-blender with a 4-quart stainless steel shell for 5 minutes and the dry blend of the immediate release layer portion was mixed with the sieved magnesium stearate in a V-blender with a 4-quart stainless steel shell for 5 minutes, separately. This lubricated blend of the extended release layer portion and the immediate release layer portion were then compressed into bi-layer tablets with the Piccola tablet press using the tooling specified in Table 10, to make the tablets of the total weight indicated.

The tablets of Examples 19-20 were tested for in vitro % release rate according to USP Procedure Drug Release USP General Chapter <711> Dissolution, using apparatus USP Type III/250 ml. The test was performed in pH 6.8, at 37° C./15 dpm. The results are shown in Table 11.

TABLE 11

| Dissolution Time (h) | Example 19(F-2) | Example 20(F-1) |
|---|---|---|
| 0 | 0 | 0 |
| 1 | 47 | 26 |
| 3 | 69 | 51 |
| 4 | 77 | 61 |
| 6 | 88 | 76 |
| 8 | 95 | 86 |
| 12 | 99 | 96 |
| Remnant | 0 | 2 |
| Recovery | 99 | 98 |

These data demonstrate that the dissolution rate from the bi-layer (ER/IR) formulation (Example 19(F-2)) was about 21% and 16% faster than the rate from the single layer (ER) formulation (Example 20(F-1)) at 1 and 4 hours time point, respectively.

Clinical Study

A Phase I, open label, five treatment arm, single dose escalation study under fasting conditions was conducted and pharmacokinetic data were obtained with the following formulations: a) the sustained delivery system-nalbuphine 60 mg bi-layer tablet (IR/ER) (Example 19 (F-2)), b) the sustained delivery system-nalbuphine 60 mg single layer tablet (ER) (Example 20(F-1)), c) two tablets of the 60 mg single layer tablet (ER, 120 mg total dose), d) three tablets of the 60 mg single layer tablet (ER, 180 mg total dose) and e) a dose of nalbuphine immediate release 60 mg oral solution (control). Eleven healthy volunteers were initially enrolled with six subjects completing all five treatments. The pharmacokinetic data are summarized below both as arithmetic and geometric mean results. The mean blood level ("plasma") concentration of nalbuphine for each time point is shown in Table 16. A logarithmic graph of the mean nalbuphine plasma concentration versus time for each formulation is shown in FIG. 1.

TABLE 12

Pharmacokinetic Parameters
Arithmetic Mean Values

| Formulation | Cmax ng/mL | *Tmax (h) | AUC(0-t) (ng * h/mL) | AUC(0-inf) (ng * h/mL) |
|---|---|---|---|---|
| 60 mg (F-2) | 8.58 | 1.5 | 75.95 | 83.87 |
| 60 mg (F-1) | 7.17 | 3.5 | 78.73 | 90.70 |
| 120 mg (F-1) | 12.87 | 6.0 | 154.63 | 170.75 |
| 180 mg (F-1) | 15.59 | 8.0 | 200.63 | 213.22 |
| 60 mg oral solution (IR) | 13.75 | 1.0 | 61.85 | 68.50 |

*Median Tmax values reported

TABLE 13

Relative Bioavailablity
(based on dose normalized arithmetic mean values)

| | Cmax ratio | AUC (0-t) ratio | AUC (0-inf) ratio |
|---|---|---|---|
| 60 mg (F-2)/ER | 0.62 | 1.23 | 1.22 |
| 60 mg (F-1)/ER | 0.52 | 1.27 | 1.32 |
| 120 mg (F-1)/ER | 0.47 | 1.25 | 1.25 |
| 180 mg (F-1)/ER | 0.38 | 1.08 | 1.04 |

TABLE 14

Pharmacokinetic Parameters
Geometric Mean Values

| Formulation | Cmax ng/mL | AUC(0-t) (ng * h/mL) | AUC(0-inf) (ng * h/mL) |
|---|---|---|---|
| 60 mg (F-2) | 7.58 | 68.72 | 77.85 |
| 60 mg (F-1) | 6.28 | 69.95 | 85.65 |
| 120 mg (F-1) | 12.24 | 140.61 | 158.62 |
| 180 mg (F-1) | 13.67 | 175.73 | 189.32 |
| 60 mg oral solution (IR) | 12.48 | 56.29 | 63.14 |

TABLE 15

Relative Bioavailablity
(based on dose normalized arithmetic mean values)

| | Cmax ratio | AUC (0-t) ratio | AUC (0-inf) ratio |
|---|---|---|---|
| 60 mg (F-2)/ER | 0.62 | 1.22 | 1.23 |
| 60 mg (F-1)/ER | 0.50 | 1.24 | 1.36 |
| 120 mg (F-1)/ER | 0.49 | 1.25 | 1.26 |
| 180 mg (F-1)/ER | 0.37 | 1.04 | 1.00 |

TABLE 16

Nalbuphine Blood Concentration
Concentration (ng/mL)

| Time Point (hrs) | 60 mg IR | 60 mg (F-1) | 60 mg (F-2) | 120 mg (F-1) | 180 mg (F1) |
|---|---|---|---|---|---|
| 0 | 0 | 0 | 0 | 0 | 0 |
| 0.25 | 10.57 | 1.83 | 0.79 | 1.01 | 1.00 |
| 0.5 | 14.81 | 4.69 | 1.71 | 2.94 | 3.55 |

TABLE 16-continued

Nalbuphine Blood Concentration
Concentration (ng/mL)

| Time Point (hrs) | 60 mg IR | 60 mg (F-1) | 60 mg (F-2) | 120 mg (F-1) | 180 mg (F1) |
|---|---|---|---|---|---|
| 1 | 13.53 | 7.57 | 3.33 | 6.51 | 7.87 |
| 1.5 | 11.20 | 7.42 | 3.63 | 8.81 | 10.59 |
| 2 | 9.77 | 6.89 | 5.88 | 9.41 | 11.40 |
| 3 | 6.58 | 6.18 | 4.96 | 9.04 | 11.90 |
| 4 | 4.65 | 5.36 | 4.77 | 8.20 | 10.71 |
| 6 | 3.29 | 5.31 | 6.18 | 10.45 | 14.01 |
| 8 | 1.76 | 4.00 | 4.76 | 8.55 | 10.59 |
| 12 | 1.67 | 2.83 | 3.32 | 6.77 | 9.20 |
| 16 | 1.01 | 1.87 | 2.24 | 4.27 | 5.14 |
| 20 | 0.76 | 1.13 | 1.51 | 2.96 | 3.27 |
| 24 | 0.68 | 0.84 | 1.11 | 2.02 | 2.46 |
| 36 | NT* | 0.57 | 0.54 | 0.94 | 0.98 |
| 48 | NT | NT | NT | NT | 0.75 |

*Not tested

In general, the F-1 (Example 20) and F-2 (Example 19) formulations had higher AUCs (0-t and 0-inf) and lower Cmax values (for both arithmetic and geometric mean values) compared to the immediate release oral solution. These differences were moderate for AUCs (0-t and 0-inf) and moderate to significant for Cmax and were based on dose-normalized comparisons of the F-1 and F-2 formulations with the immediate release oral solution. Minimal differences in AUCs (0-t and 0-inf) were seen between the F-1 and F-2 formulations at a comparative dose of 60 mg.

These data demonstrate that the oral bioavailability for the sustained release nalbuphine formulations was greater than that of the immediate release control formulation. Specifically, the oral availability of formulation F-2 was 23% greater than that of the immediate release oral solution, based on the geometric mean values for the area under the plasma concentration time curve. Similarly, the oral bioavailability of Formulation FI was 36% greater than that of the immediate release oral solution, based on the geometric mean values for the area under the plasma concentration time curve.

The Cmax values for the sustained release formulations were approximately 60% of the Cmax observed with the immediate release oral solution. These data suggest that the potential for adverse events (i.e., side effects) could be decreased with the sustained release formulation compared to immediate release formulations.

Median Tmax values reported were 1.0, 1.5 and 3.5 hours for the oral solution, F-2 and F-1 formulations, respectively. Longer Tmax values were observed for the 2 higher doses of the F-1 formulation (6.0 and 8.0 hours for the 120 and 180 mg doses, respectively).

Dose linearity was observed for all three doses of the F-1 formulation (60, 120 and 180 mg.

As shown in FIG. 1, the blood serum concentration of nalbuphine for the extended release formulations increases quickly to one or more peaks shortly following administration, followed by a plateau region. The duration of the plateau period varies based on the dose strength and type of formulation, but is generally in the range from about 1.5 hours to about 10 hours. In contrast, the blood serum level for the immediate release formulation quickly maximizes, followed by an immediate decrease in nalbuphine concentration from time point to time point. Following the plateau period, there is a decrease in the nalbuphine blood plasma concentration from one time point to the next.

Example 21

Phase IIa Trial

A pilot Phase IIa trial pharmacokinetic-pharmacodynamic (PK-PD) investigation was designed to correlate the level of analgesia in patients with the plasma level of nalbuphine in an extended release (sustained release) formulation (nalbuphine ER). This trial was conducted to determine if there is an exposure-response relationship, as well as to determine the duration of analgesia.

The nalbuphine ER formulation used in the study is represented by that described in Table 10, Example 19. The formulation was expected to have plasma kinetics derived from both immediate release and controlled release components of the formulation. The formulation was a bilayered tablet (Geminex®, Penwest Pharmaceuticals Co., Danbury Conn.) in which one layer was a controlled release formulation using TIMERx® technology (Penwest Pharmaceuticals Co., Danbury, Conn.). The other layer was formulated for immediate release of nalbuphine.

Patients in the trial underwent third molar extractions, a commonly used clinical pain model for evaluating the acute effectiveness of analgesics. Under the protocol, patients who experienced at least a score of four on the 0-to-10 NPRS pain scale following completion of their dental procedures received blinded study medication of 60 mg nalbuphine ER, 120 mg nalbuphine ER, or placebo as a single dose. Pain relief was then evaluated at pre-specified intervals over the 12-hour period following dosing. Blood samples were also collected at pre-specified intervals for 24 hours post-dose to determine plasma concentrations of nalbuphine. Patients were allowed to take rescue medication (ibuprofen, 800 mg) if needed. Pain assessments were carried out for up to and including 12 hours in all patients, regardless of use of rescue medication. One hundred sixty-five patients were tested in the study.

A summary of the pharmacokinetic parameters from the Phase IIa trial are provided below in Table 17.

TABLE 17

Pharmacokinetic Parameters

| Dose Group | Statistic | Cmax (ng/mL) | Tmax (hr) | AUC (ng * hr/mL) |
|---|---|---|---|---|
| 60 mg | N | 65 | 65 | 65 |
| | Mean | 8.1 | 4.5 | 75.2 |
| | SD | 4.9 | 2.2 | 45.2 |
| | Median | 6.6 | 6 | 65.3 |
| 120 mg | N | 66 | 66 | 66 |
| | Mean | 16.4 | 4.3 | 149.2 |
| | SD | 10.6 | 2.7 | 77.0 |
| | Median | 13.2 | 3 | 128.3 |

Results reported herein demonstrate that nalbuphine positively reduced the pain intensity in a dose-dependent manner over 12 hours (Table 18). Differences from placebo began at 90 minutes post-dose for the higher strength and at 6 hours for the lower strength, and were maintained at all time points over the remaining 12 hour dosing interval. Pain intensity was assessed using an 11-point (0 to 10) numeric pain rating scale, ranging from "no pain" to "pain as bad as can be imagined".

TABLE 18

Pain Intensity for Nalbuphine 60-mg and 120-mg Formulations Compared to Placebo

| Timepoint | Placebo | | | 60 mg | | | | 20 mg | | | |
|---|---|---|---|---|---|---|---|---|---|---|---|
| (hrs postdose | Mean | SD | Median | Mean | SD | Median | p-value* | Mean | SD | Median | p-value* |
| 0 (baseline) | 6.1 | 1.6 | 6.0 | 6.2 | 1.4 | 6.0 | 0.2964 | 6.0 | 1.5 | 6.0 | |
| 0.25 | 5.8 | 1.7 | 6.0 | 6.2 | 1.5 | 6.0 | 0.2964 | 6.0 | 1.5 | 6.0 | 0.5265 |
| 0.50 | 5.9 | 2.0 | 6.0 | 6.1 | 1.8 | 6.0 | 0.7864 | 5.7 | 1.9 | 6.0 | 0.9382 |
| 0.75 | 6.0 | 2.2 | 7.0 | 5.9 | 2.0 | 6.0 | 0.8848 | 5.2 | 2.3 | 5.0 | 0.0963 |
| 1 | 6.3 | 2.4 | 7.0 | 5.9 | 2.1 | 6.0 | 0.4937 | 5.3 | 2.4 | 5.0 | 0.0621 |
| 1.5 | 6.7 | 2.5 | 7.0 | 6.0 | 2.3 | 6.0 | 0.2146 | 5.3 | 2.6 | 6.0 | 0.0152 |
| 2 | 6.6 | 2.6 | 7.0 | 5.9 | 2.7 | 6.0 | 0.2856 | 5.3 | 2.6 | 5.5 | 0.0330 |
| 3 | 6.6 | 2.7 | 7.0 | 5.7 | 2.7 | 5.0 | 0.1536 | 5.3 | 3.0 | 5.5 | 0.0486 |
| 4 | 6.6 | 2.7 | 7.0 | 5.4 | 3.0 | 5.0 | 0.0828 | 5.1 | 3.1 | 5.0 | 0.0330 |
| 5 | 6.6 | 2.8 | 7.0 | 5.3 | 3.1 | 5.0 | 0.0750 | 5.1 | 3.2 | 5.0 | 0.0326 |
| 6 | 6.7 | 2.6 | 7.0 | 5.2 | 3.1 | 5.0 | 0.0406 | 4.9 | 3.3 | 5.0 | 0.0138 |
| 7 | 6.7 | 2.6 | 7.0 | 5.1 | 3.2 | 5.0 | 0.0283 | 4.8 | 3.3 | 5.0 | 0.0093 |
| 8 | 6.6 | 2.7 | 7.0 | 5.2 | 3.2 | 5.0 | 0.0466 | 4.8 | 3.3 | 5.0 | 0.0126 |
| 9 | 6.8 | 2.6 | 7.0 | 5.1 | 3.2 | 5.0 | 0.0222 | 4.8 | 3.3 | 5.0 | 0.0083 |
| 10 | 6.9 | 2.5 | 7.0 | 5.1 | 3.3 | 5.0 | 0.0117 | 4.9 | 3.3 | 5.0 | 0.0090 |
| 11 | 6.9 | 2.4 | 7.0 | 5.3 | 3.1 | 5.0 | 0.0235 | 4.9 | 3.3 | 5.0 | 0.0057 |
| 12 | 6.8 | 2.5 | 7.0 | 5.3 | 3.1 | 5.0 | 0.0371 | 4.8 | 3.4 | 5.0 | 0.0047 |

*Dunnet p-value comparing each treatment group with placebo at eachtime point

Patients who received active treatment had a higher mean pain relief score up to 12 hours postdose compared with those who received placebo. A 5-point pain relief scale was used by patients to subjectively assess their level of pain relief by responding to the question "How much relief do you have from your starting pain?" where 0 corresponded to no relief and 4 corresponded to complete relief. As shown in Table 19, high scores were relatively consistent between the low and high dose groups. In addition, pain relief occurred earlier in the high dose group (0.75 hours postdose) compared with the low dose group (4 hours postdose).

TABLE 19

Pain Relief Rating for Nalbuphine 60-mg and 120-mg Formulations Compared to Placebo

| Timepoint | Placebo | | | 60 mg | | | | 120 mg | | | |
|---|---|---|---|---|---|---|---|---|---|---|---|
| (hrs postdose | Mean | SD | Median | Mean | SD | Median | p-value* | Mean | SD | Median | p-value* |
| 0 (baseline) | 0.4 | 0.6 | 0.0 | 0.4 | 0.6 | 0 | 1.0 | 0.3 | 0.5 | 0 | 0.8665 |
| 0.50 | 0.5 | 0.8 | 0 | 0.6 | 0.8 | 0 | 0.7430 | 0.6 | 0.8 | 0 | 0.7200 |
| 0.75 | 0.5 | 0.9 | 0 | 0.8 | 0.9 | 1.0 | 0.2510 | 1.1 | 1.0 | 1.0 | 0.0163 |
| 1 | 0.5 | 0.9 | 0 | 0.9 | 1.0 | 1.0 | 0.1994 | 1.0 | 1.1 | 1.0 | 0.0431 |
| 1.5 | 0.4 | 0.8 | 0 | 0.8 | 1.0 | 0 | 0.1589 | 1.2 | 1.2 | 1.0 | 0.0027 |
| 2 | 0.5 | 0.9 | 0 | 0.9 | 1.1 | 0.0 | 0.1573 | 1.2 | 1.1 | 1.0 | 0.0035 |
| 3 | 0.6 | 1.0 | 0 | 1.1 | 1.2 | 1.0 | 0.0884 | 1.3 | 1.3 | 1.0 | 0.0131 |
| 4 | 0.6 | 1.0 | 0 | 1.2 | 1.3 | 1.0 | 0.0301 | 1.3 | 1.4 | 1.0 | 0.0174 |
| 5 | 0.6 | 1.0 | 0 | 1.3 | 1.3 | 1.0 | 0.0254 | 1.4 | 1.4 | 1.0 | 0.0073 |
| 6 | 0.5 | 1.0 | 0 | 1.3 | 1.4 | 1.0 | 0.0142 | 1.4 | 1.5 | 1.5 | 0.0036 |
| 7 | 0.5 | 0.9 | 0 | 1.4 | 1.4 | 1.0 | 0.0071 | 1.5 | 1.5 | 1.5 | 0.0017 |
| 8 | 0.6 | 1.1 | 0 | 1.4 | 1.4 | 1.0 | 0.0203 | 1.5 | 1.5 | 1.0 | 0.0091 |
| 9 | 0.6 | 1.0 | 0 | 1.4 | 1.4 | 1.0 | 0.0182 | 1.4 | 1.5 | 1.0 | 0.0079 |
| 10 | 0.5 | 0.9 | 0 | 1.5 | 1.5 | 1.0 | 0.0032 | 1.5 | 1.5 | 1.0 | 0.0018 |
| 11 | 0.5 | 0.9 | 0 | 1.4 | 1.4 | 1.0 | 0.0092 | 1.4 | 1.5 | 1.0 | 0.0018 |
| 12 | 0.5 | 0.8 | 0 | 1.4 | 1.4 | 1.0 | 0.0137 | 1.5 | 1.5 | 1.0 | 0.0012 |

*Dunnet p-value comparing each treatment group with placebo at eachtime point

Patients were allowed to take rescue medication if needed, but were encouraged to wait at least 2 hours before taking it. For patients receiving placebo, the median time to taking rescue medication was 2.3 hours, compared to a median time to taking rescue medication of 3.3 hours and 6.0 hours for patients receiving 60 mg and 120 mg nalbuphine, respectively. These data demonstrate the time to ingestion of rescue medication was significantly longer at the low and high nalbuphine doses, respectively, compared to placebo. Moreover, the proportion of patients requiring rescue analgesic therapy during the 12-hour study period was significantly lower with the two nalbuphine treatments compared to placebo: 55% of patients who received the 120 mg dose and 62% of patients who received the 60 mg dose took rescue medication within 12 hours of receiving treatment, compared to 88% of patients who received placebo.

The percentage of patients experiencing at least a 50% reduction in pain intensity was significantly higher and for the low and high nalbuphine dose groups (55% and 48% reporting a 50% reduction in pain intensity, respectively) compared to placebo (26% reporting a 50% reduction in pain intensity). No unusual side effects were reported during the 12 hour dosing interval. No differences in side effect intensity among the three study treatments were noted at the end of the 12 hour study.

Example 22

Nalbuphine 60 mg Extended Release Tablets

The 60 mg extended release nalbuphine tablets of Example 22 were prepared as follows: Nalbuphine HCl and TIMERx M30A were added to a high shear mixer and dry mixed at low speed. A granulating solution (water for injection or purified water) was then introduced to the mixer at low speed. The subsequent mixture was granulated at high speed and dried in a fluid bed processor. The dried granules were milled and sized via a conventional mill. The milled granulation was then transferred into a diffusion (tumble) mixer. Magnesium stearate was added to the diffusion mixer and blended. The final blend was compressed using a rotary tablet press. The resulting tablets were then coated with the non-functional coating using a conventional coating pan.

TABLE 20

60 mg Extended Release Nalbuphine Tablet with Non-Functional Coating

| Ingredient | mg/tablet |
| --- | --- |
| Nalbuphine HCl | 60.0 |
| TIMERx M30A[1] | 150.0 |
| (Mannitol) | (90.0) |
| (Locust bean gum) | (27.0) |
| (Xanthan Gum) | (18.0) |
| (Calcium sulfate dihydrate) | (15.0) |
| Magnesium stearate | 1.1 |
| Opadry II Purple | 6.3 |
| Water for injection or Purified water | QS |
| Total: | 217.4 |

[1]Sustained release excipient of Example 2

The formulation of Example 22 is identical to the tablet formulation of Examples 9 and 20, except with the addition of a non-functional coating.

Example 23

Nalbuphine 60 mg Extended Release Tablets

The 60 mg extended release nalbuphine tablets of Example 23 were prepared as follows: Nalbuphine HCl and TIMERx M30A were added to a high shear mixer and dry mixed at low speed. A granulating solution (water for injection or purified water) was then introduced to the mixer at low speed. The subsequent mixture was granulated at high speed and dried in a fluid bed processor. The dried granules were milled and sized via a conventional mill. The milled granulation was then transferred into a diffusion (tumble) mixer. Hydroxypropyl cellulose was added to the diffusion mixer and blended. Thereafter, magnesium stearate was added to the diffusion mixer and blended. The final blend was compressed using a rotary tablet press. The resulting tablets were then coated with the non-functional coating using a conventional coating pan.

TABLE 21

60 mg Extended Release Nalbuphine Tablet with Addition of Hydroxypropyl Cellulose and Reduction of TimeRx Excipient

| Ingredient | mg/tablet |
| --- | --- |
| Nalbuphine HCl | 60.0 |
| TIMERx M30A[1] | 120.0 |
| (Mannitol) | (72.0) |
| (Locust bean gum) | (21.6) |
| (Xanthan Gum) | (14.4) |
| (Calcium sulfate dihydrate) | (12.0) |
| Hydroxypropylcellulose | 30.0 |
| Magnesium stearate | 1.6 |
| Water for injection or Purified water | QS |
| Total: | 211.6 |

[1]Sustained release excipient of Example 2

Examples 24-28

The nalbuphine tablets of Examples 24-28 were prepared as follows: Nalbuphine HCl, mannitol, xanthan gum, locust bean gum and calcium sulfate dihydrate were added to a high shear mixer and dried mix at low speed. A granulating solution (water for injection or purified water) was introduced into the mixer at low speed. The wet granulation was granulated at high speed and dried in a fluid bed processor. The dried granules were milled and sized using a conventional mill. The milled granulation was transferred into a diffusion (tumble) mixer. Hydroxypropylcellulose and, when applicable, fumaric acid (180 mg formulations only) were added to the diffusion mixer and blended. Thereafter, magnesium stearate was added to the diffusion mixer and blended. The final blend was compressed using a rotary tablet press.

TABLE 22

(Example 24)
30 mg Extended Release Nalbuphine Tablet

| Ingredient | mg/tablet |
| --- | --- |
| Nalbuphine HCl | 30.0 |
| Mannitol | 108.0 |
| Hydroxypropylcellulose | 35.0 |
| Locust bean gum | 32.4 |
| Xanthan gum | 21.6 |
| Calcium sulfate dehydrate | 18.0 |
| Magnesium stearate | 1.9 |
| Water for injection or Purified water | QS |
| Total: | 246.9 |

TABLE 23

(Example 25)
60 mg Extended Release Nalbuphine Tablet

| Ingredient | mg/tablet |
| --- | --- |
| Nalbuphine HCl | 60.0 |
| Mannitol | 72.0 |
| Hydroxypropylcellulose | 30.0 |
| Locust bean gum | 21.6 |
| Xanthan gum | 14.4 |
| Calcium sulfate dehydrate | 12.0 |
| Magnesium stearate | 1.6 |
| Water for injection or Purified water | QS |
| Total: | 211.6 |

TABLE 24

(Example 26)
120 mg Extended Release Nalbuphine Tablet

| Ingredient | mg/tablet |
| --- | --- |
| Nalbuphine HCl | 120.0 |
| Mannitol | 144.0 |
| Hydroxypropylcellulose | 60.0 |
| Locust bean gum | 43.2 |
| Xanthan gum | 28.8 |
| Calcium sulfate dehydrate | 24.0 |
| Magnesium stearate | 3.2 |
| Water for injection or Purified water | QS |
| Total: | 423.2 |

TABLE 25

(Example 27)
180 mg Extended Release Nalbuphine Tablet (release 1)

| Ingredient | mg/tablet |
| --- | --- |
| Nalbuphine HCl | 180.0 |
| Mannitol | 216.0 |
| Hydroxypropylcellulose | 90.0 |
| Locust bean gum | 64.8 |
| Xanthan gum | 43.2 |
| Fumaric acid | 25.0 |
| Calcium sulfate dehydrate | 36.0 |
| Magnesium stearate | 5.0 |
| Water for injection or Purified water | QS |
| Total: | 660.0 |

TABLE 26

(Example 28)
180 mg Extended Release Nalbuphine Tablet (release 2)

| Ingredient | mg/tablet |
| --- | --- |
| Nalbuphine HCl | 180.0 |
| Mannitol | 162.0 |
| Hydroxypropylcellulose | 60.0 |
| Locust bean gum | 48.6 |
| Xanthan gum | 32.4 |
| Fumaric acid | 25.0 |
| Calcium sulfate dehydrate | 27.0 |
| Magnesium stearate | 4.0 |
| Water for injection or Purified water | QS |
| Total: | 539.0 |

Example 29

A Phase II, randomized, double-blind, single-dose, placebo-controlled, multi-center, parallel group study of the safety and efficacy of the nalbuphine bi-layer tablet formulation of Example 19 was conducted. Study subjects were randomized to active agent received either a single 60 mg extended release dose of nalbuphine or a single 120 mg (2×60 mg tablets) dose of nalbuphine. Table 27A-B provides a summary of the observed pharmacokinetic parameters.

TABLE 27A (60 mg single dose)

| Statistic | Cmax (ng/ml) | Tmax (hr) | AUC (ng * hr/ml) |
| --- | --- | --- | --- |
| N | 65 | 65 | 65 |
| Mean | 8.1 | 4.5 | 75.2 |
| SD | 4.9 | 2.2 | 45.2 |
| minimum | 3.0 | 0.5 | 23.6 |
| median | 6.6 | 6 | 65.3 |
| maximum | 22.3 | 12 | 256.6 |
| % CV | 60.4% | 48.5% | 60.1% |
| Geometric mean | 6.9 | 3.9 | 64.8 |

TABLE 27B (120 mg single dose)

| Statistic | Cmax (ng/ml) | Tmax (hr) | AUC (ng * hr/ml) |
| --- | --- | --- | --- |
| N | 66 | 66 | 66 |
| Mean | 16.4 | 4.3 | 149.2 |
| SD | 10.6 | 2.7 | 77.0 |
| minimum | 4.6 | 0.5 | 33.2 |
| median | 13.2 | 3 | 128.3 |
| maximum | 77.4 | 12 | 450.2 |
| % CV | 64.9% | 63.8% | 51.6% |
| Geometric mean | 14.1 | 3.4 | 133.1 |

Example 30

A Phase I, randomized single dose, four period cross-over study to evaluate the effect of food on two nalbuphine extended release tablet formulations (bi-layer formulation of Example 19 and extended release formulation of Example 20) administered orally to healthy subjects under fed and fasted conditions was conducted. The total single dose administered to each study subject was 120 mg (2×60 mg tablets). Table 28 provides a summary of the observed pharmacokinetic parameters.

TABLE 28

| Treatment | Statistics | $C_{max}$ (ng/mL) | $T_{max}$ (hr) | $AUC_{(0-last)}$ (ng * hr/mL) | $AUC_{(0-inf)}$ (ng * hr/mL) |
| --- | --- | --- | --- | --- | --- |
| Formula of Example 20 120 mg Fast | N | 9 | 9 | 9 | 9 |
| | Mean | 14.1 | — | 170 | 183 |
| | SD | 6.23 | — | 59.7 | 62.9 |
| | Min | 4.57 | 1.50 | 56.7 | 61.6 |
| | Median | 15.1 | 6.00 | 179 | 195 |
| | Max | 23.6 | 12.00 | 245 | 256 |
| Formula of Example 20 120 mg Fed | N | 9 | 9 | 9 | 9 |
| | Mean | 22.4 | — | 201 | 211 |
| | SD | 12.7 | — | 67.2 | 68.3 |
| | Min | 8.77 | 3.00 | 70.2 | 73.9 |
| | Median | 21.0 | 6.00 | 219 | 227 |
| | Max | 48.6 | 10.00 | 295 | 307 |
| Formula of Example 19 120 mg Fast | N | 9 | 9 | 9 | 9 |
| | Mean | 18.5 | — | 160 | 170 |
| | SD | 7.40 | — | 55.6 | 54.7 |
| | Min | 6.63 | 1.00 | 81.5 | 87.7 |
| | Median | 18.6 | 2.00 | 178 | 186 |
| | Max | 28.7 | 6.00 | 239 | 250 |
| Formula of Example 19 120 mg Fed | N | 9 | 9 | 9 | 9 |
| | Mean | 28.0 | — | 204 | 214 |
| | SD | 16.6 | — | 68.6 | 71.0 |
| | Min | 11.0 | 2.00 | 98.2 | 111 |
| | Median | 24.0 | 6.00 | 227 | 237 |
| | Max | 63.7 | 6.00 | 279 | 295 |

Example 31

A Phase I, randomized, single dose, four period, cross-over study to evaluate the intra-subject variability of two nalbuphine extended release formulations (bi-layer formulation of Example 19 and extended release formulation of Example 20) administered orally to healthy subjects under fasted conditions was conducted. The total single dose administered to each study subject was 120 mg (2×60 mg tablets). Table 29 provides a summary of the observed pharmacokinetic parameters.

TABLE 29

| Treatment | Statistics | $C_{max}$ (ng/mL) | $T_{max}$ (hr) | $AUC_{(0-last)}$ (ng * hr/mL) | $AUC_{(0-inf)}$ (ng * hr/mL) |
|---|---|---|---|---|---|
| ERF-1 (A1) | N | 7 | 7 | 7 | 6 |
| | Mean | 11.3 | — | 139 | 162 |
| | SD | 7.17 | — | 75.0 | 78.8 |
| | Minimum | 3.08 | 2.00 | 39.0 | 47.0 |
| | Median | 12.1 | 6.00 | 157 | 173 |
| | Maximum | 20.5 | 12.00 | 257 | 279 |
| ERF-1 (A2) | N | 7 | 7 | 7 | 6 |
| | Mean | 13.4 | — | 152 | 167 |
| | SD | 8.81 | — | 73.5 | 80.9 |
| | Minimum | 3.70 | 1.50 | 44.7 | 57.3 |
| | Median | 12.3 | 6.00 | 128 | 156 |
| | Maximum | 30.2 | 8.00 | 252 | 263 |
| ERF-2 (C1) | N | 7 | 7 | 7 | 6 |
| | Mean | 14.2 | — | 148 | 170 |
| | SD | 8.87 | — | 78.3 | 78.2 |
| | Minimum | 4.41 | 1.50 | 39.7 | 51.5 |
| | Median | 8.57 | 6.00 | 123 | 176 |
| | Maximum | 26.6 | 8.00 | 259 | 265 |
| ERF-2 (C2) | N | 7 | 7 | 7 | 6 |
| | Mean | 12.5 | — | 137 | 155 |
| | SD | 8.02 | — | 77.5 | 78.9 |
| | Minimum | 4.88 | 1.00 | 44.6 | 49.8 |
| | Median | 9.17 | 2.00 | 142 | 161 |
| | Maximum | 26.3 | 10.00 | 270 | 277 |

Example 32

A phase I, randomized, single-blind, placebo-controlled, multiple ascending dose tolerance trial of nalbuphine extended release tablets (of Example 22) in healthy adult subjects in the fasted state. Table 30 and 31 provides a summary of the observed pharmacokinetic parameters.

TABLE 30

Single Dose Administration Pharmacokinetic Data

| Parameter | Statistics | 60 mg Period 1 | 120 mg Period 2 | 180 mg Period 3 | 180 mg Period 4 |
|---|---|---|---|---|---|
| Cmax | N | 3 | 5 | 3 | 5 |
| (ng/mL) | Mean | 7.920 | 15.574 | 27.800 | 23.420 |
| | SD | 1.4722 | 8.4070 | 9.9000 | 10.6302 |
| | Median | 7.360 | 14.900 | 27.800 | 21.600 |
| | Min | 6.81 | 5.47 | 17.90 | 10.30 |
| | Max | 9.59 | 27.80 | 37.70 | 39.80 |
| Tmax (hr) | N | 3 | 5 | 3 | 5 |
| | Mean | 5.67 | 3.60 | 5.67 | 3.00 |
| | SD | 1.155 | 2.074 | 0.577 | 2.000 |
| | Median | 5.00 | 4.00 | 6.00 | 3.00 |
| | Min | 5.0 | 1.0 | 5.0 | 1.0 |
| | Max | 7.0 | 6.0 | 6.0 | 5.0 |

TABLE 31

Multiple Doses Pharmacokinetic Data

| Treatment | Statistics | 60 mg Period 1 | 120 mg Period 2 | 180 mg Period 3 | 180 mg Period 4 |
|---|---|---|---|---|---|
| Cmax, ss | N | 3 | 5 | 3 | 5 |
| (ng/mL) | Mean | 12.10 | 18.76 | 32.17 | 29.58 |
| | SD | 1.217 | 1.806 | 8.810 | 11.107 |
| | Median | 11.50 | 19.00 | 29.10 | 27.40 |
| | Min | 11.3 | 15.9 | 25.3 | 18.4 |
| | Max | 13.5 | 20.6 | 42.1 | 46.7 |
| Tmax, ss(hr) | N | 3 | 5 | 3 | 5 |
| | Mean | 5.00 | 3.40 | 4.33 | 5.60 |
| | SD | 1.000 | 2.074 | 3.215 | 0.894 |
| | Median | 5.00 | 3.00 | 3.00 | 5.00 |
| | Min | 4.0 | 1.0 | 2.0 | 5.0 |
| | Max | 6.0 | 6.0 | 8.0 | 7.0 |
| Cmin, ss | N | 3 | 5 | 3 | 5 |
| (ng/mL) | Mean | 3.263 | 5.974 | 12.067 | 7.232 |
| | SD | 0.7966 | 0.9232 | 1.6653 | 2.1101 |
| | Median | 3.450 | 6.300 | 12.600 | 7.440 |
| | Min | 2.39 | 4.85 | 10.20 | 4.84 |
| | Max | 3.95 | 7.08 | 13.40 | 10.20 |

Example 33

A phase I, randomized, single dose, five-period cross-over study in healthy subjects to evaluate the intra-subject variability of a nalbuphine extended release tablet formulation (of Example 23). Table 32 provides a summary of the observed pharmacokinetic parameters.

TABLE 32

| Parameter | Statistics | Treatment A1 | Treatment A2 | 120 mg (Fast) Treatment A | 120 mg (Fed) Treatment B | Oral Solution Treatment C | Oral Solution Treatment D |
|---|---|---|---|---|---|---|---|
| Cmax | N | 12 | 12 | 12 | 12 | 12 | 12 |
| (ng/mL) | Mean | 12.498 | 12.903 | 12.700 | 18.549 | 18.503 | 16.863 |
| | SD | 7.1308 | 5.4062 | 5.7697 | 10.6560 | 7.8579 | 6.7619 |
| | Median | 12.100 | 13.300 | 11.370 | 15.950 | 17.100 | 14.950 |
| | Min | 4.03 | 3.83 | 3.93 | 5.79 | 8.53 | 8.62 |
| | Max | 32.30 | 20.30 | 26.30 | 41.90 | 36.30 | 31.40 |
| Tmax (hr) | N | 12 | 12 | 12 | 12 | 12 | 12 |
| | Mean | 5.250 | 5.167 | 5.208 | 4.625 | 0.750 | 2.817 |
| | SD | 3.4411 | 2.6572 | 2.3400 | 2.0352 | 0.3371 | 0.8055 |
| | Median | 3.500 | 6.000 | 5.750 | 6.000 | 0.500 | 1.900 |
| | Min | 2.00 | 1.00 | 2.00 | 1.50 | 0.50 | 1.00 |
| | Max | 12.00 | 8.00 | 10.00 | 6.00 | 1.50 | 4.00 |
| AUC (0-last) | N | 12 | 12 | 12 | 12 | 12 | 12 |
| (ng*hr/mL) | Mean | 159.450 | 154.391 | 156.921 | 169.723 | 83.793 | 103.154 |
| | SD | 60.2859 | 59.9296 | 54.7635 | 70.0775 | 24.1551 | 27.2275 |
| | Median | 155.720 | 151.944 | 158.828 | 168.859 | 84.097 | 101.217 |

TABLE 32-continued

| Parameter | Statistics | Treatment A1 | Treatment A2 | 120 mg (Fast) Treatment A | 120 mg (Fed) Treatment B | Oral Solution Treatment C | Oral Solution Treatment D |
|---|---|---|---|---|---|---|---|
| | Min | 56.97 | 54.32 | 55.65 | 56.76 | 51.24 | 63.89 |
| | Max | 260.41 | 274.17 | 267.29 | 282.63 | 143.74 | 147.43 |
| AUC (0-inf) | N | 8 | 8 | 8 | 8 | 8 | 8 |
| (ng*hr/mL) | Mean | 160.790 | 161.532 | 161.161 | 170.590 | 85.926 | 103.053 |
| | SD | 61.1655 | 54.6973 | 51.8638 | 69.3711 | 13.6623 | 29.5312 |
| | Median | 152.985 | 166.487 | 167.257 | 162.708 | 90.056 | 96.558 |
| | Min | 64.80 | 63.01 | 63.91 | 66.16 | 63.66 | 70.24 |
| | Max | 238.44 | 258.27 | 213.18 | 272.16 | 104.20 | 151.97 |

Example 34

A phase I, open-label, single dose, five-period cross-over study to determine the dose proportionality of 30, 60, 120 and 180 mg nalbuphine extended release tablet formulations (of Examples 24-28). Table 33A-E provides a summary of the observed pharmacokinetic parameters for the 60 mg, 120 mg and 180 mg formulations of Examples 25, 26, 27 and 28, respectively.

TABLE 33A

| Treatment Description | Parameter | $T_{max}$ (hr) N = 22 | $C_{max}$ (ng/mL) N = 22 | $AUC_{last}$ (hr * ng/mL) N = 22 | $AUC_{INF}$ (hr * ng/mL) N = 19 |
|---|---|---|---|---|---|
| 30 mg nalbuphine HCl ER tablet | Mean | 4.159 | 4.130 | 42.988 | 54.993 |
| | SD | 1.996 | 2.338 | 20.135 | 20.681 |
| | Min | 1.50 | 1.95 | 21.26 | 27.35 |
| | Median | 3.00 | 3.82 | 39.99 | 53.13 |
| | Max | 8.00 | 12.70 | 110.41 | 117.08 |

TABLE 33B

| Treatment Description | Parameter | $T_{max}$ (hr) N = 24 | $C_{max}$ (ng/mL) N = 24 | $AUC_{last}$ (hr * ng/mL) N = 24 | $AUC_{INF}$ (hr * ng/mL) N = 23 |
|---|---|---|---|---|---|
| 60 mg nalbuphine HCl ER tablet | Mean | 7.417 | 7.750 | 94.496 | 108.798 |
| | SD | 2.962 | 6.034 | 40.001 | 38.737 |
| | Min | 3.00 | 2.84 | 37.56 | 50.73 |
| | Median | 6.00 | 6.07 | 89.31 | 103.12 |
| | Max | 12.00 | 29.90 | 186.60 | 196.41 |

TABLE 33C

| Treatment Description | Parameter | $T_{max}$ (hr) N = 19 | $C_{max}$ (ng/mL) N = 19 | $AUC_{last}$ (hr * ng/mL) N = 19 | $AUC_{INF}$ (hr * ng/mL) N = 18 |
|---|---|---|---|---|---|
| 120 mg nalbuphine HCl ER tablet | Mean | 6.316 | 13.265 | 192.434 | 208.312 |
| | SD | 2.709 | 6.458 | 82.867 | 90.778 |
| | Min | 1.00 | 6.54 | 81.41 | 105.82 |
| | Median | 6.00 | 12.80 | 197.01 | 205.96 |
| | Max | 12.00 | 34.80 | 463.17 | 503.93 |

TABLE 33D

| Treatment Description | Parameter | $T_{max}$ (hr) N = 15 | $C_{max}$ (ng/mL) N = 15 | $AUC_{last}$ (hr * ng/mL) N = 15 | $AUC_{INF}$ (hr * ng/mL) N = 15 |
|---|---|---|---|---|---|
| 180 mg nalbuphine | Mean | 7.600 | 21.559 | 297.460 | 327.842 |
| | SD | 3.043 | 23.526 | 154.701 | 164.674 |

TABLE 33D-continued

| Treatment Description | Parameter | $T_{max}$ (hr) N = 15 | $C_{max}$ (ng/mL) N = 15 | $AUC_{last}$ (hr * ng/mL) N = 15 | $AUC_{INF}$ (hr * ng/mL) N = 15 |
|---|---|---|---|---|---|
| HCl ER tablet (release 1) | Min | 2.00 | 5.89 | 138.35 | 148.67 |
| | Median | 6.00 | 16.30 | 274.64 | 288.86 |
| | Max | 12.00 | 102.00 | 722.79 | 760.86 |

TABLE 33E

| Treatment Description | Parameter | $T_{max}$ (hr) N = 19 | $C_{max}$ (ng/mL) N = 19 | $AUC_{last}$ (hr * ng/mL) N = 19 | $AUC_{INF}$ (hr * ng/mL) N = 18 |
|---|---|---|---|---|---|
| 180 mg nalbuphine HCl ER tablet (release 2) | Mean | 8.000 | 19.182 | 318.759 | 339.507 |
| | SD | 4.604 | 11.007 | 167.371 | 117.176 |
| | Min | 1.00 | 8.25 | 151.52 | 156.52 |
| | Median | 6.00 | 17.60 | 280.56 | 291.71 |
| | Max | 16.00 | 56.40 | 877.38 | 909.86 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A sustained release oral solid dosage form comprising nalbuphine or a pharmaceutically acceptable salt thereof in a gel matrix sustained release delivery system, wherein the dosage form providing an onset of nalbuphine effect from about 30 minutes of dosing to within about 6 hours of dosing and a controlled release of the nalbuphine over a time period of at least about 8 hours, in the form of a tablet.

2. The dosage form of claim 1, which provides a $C_{max}$ from about 1.95 to about 102.00 ng/ml in a healthy human subject.

3. The dosage form of claim 1, which provides a Tmax at about 1.00 hour to about 16 hours after administration of the dosage form to a healthy human subject.

4. The dosage form of claim 1, wherein the median $T_{max}$ ranges from about 1.5 to about 8.0 hours after administration of the dosage form to healthy human subjects.

5. The dosage form of claim 1, wherein the sustained release delivery system comprises at least one hydrophilic compound in an amount from about 5% to about 80% by weight.

6. The dosage form of claim 1, which is in the form of a tablet, wherein the sustained release delivery system comprises at least one hydrophilic compound in an amount from about 5% to about 80% by weight and at least one pharmaceutical diluent.

7. The dosage form of claim 1, wherein the sustained release delivery system comprises a compound selected from gums, cellulose ethers, acrylic resins, polyvinyl pyrrolidone, protein-derived compounds, and mixtures thereof.

8. The dosage form of claim 1, wherein the gel matrix comprises a gum selected from xanthan, tragacanth, pectins, acacia, karaya, alginates, agar, guar, hydroxypropyl guar, carrageenan, locust bean gums, gellan gums, hydroxyalkyl celluloses, carboxyalkyl celluloses, and mixtures thereof.

9. The dosage form of claim 1, which comprises from about 1 mg to about 200 mg nalbuphine hydrochloride.

10. The dosage form of claim 9, wherein the sustained release delivery system comprises about 10 mg to about 420 mg.

11. The dosage form of claim 1, which provides a mean $C_{max}$ from about 4.130 to about 32.17 ng/ml in healthy human subjects.

12. The dosage form of claim 1, wherein the median $T_{max}$ ranges from about 1.5 to about 8.0 hours after administration of the dosage form to healthy human subjects.

13. A sustained release oral tablet comprising nalbuphine or a pharmaceutically acceptable salt thereof homogeneously dispersed in a sustained release delivery system selected from the group consisting of gums, cellulose ethers, acrylic resins, polyvinyl pyrrolidone, protein-derived compounds, and mixtures thereof, and at least one pharmaceutical diluent, the tablet providing an onset of nalbuphine effect from about 30 minutes of dosing to within about 6 hours of dosing and a release of the nalbuphine over a time period of at least about 8 hours.

14. The sustained release oral tablet of claim 1, comprising a sustained release film including a release-modifying compound.

15. The sustained release oral tablet of claim 1, wherein the dosage form maintains a plateau of a relatively constant blood serum level of nalbuphine during a dosage interval of about 1 hours to about 12 hours.

16. The sustained release oral tablet of claim 15, wherein the plateau has a duration of about 2 to about 10 hours.

17. The sustained release oral tablet of claim 15, wherein the plateau has a duration of about 6 hours to about 9 hours.

18. The sustained release oral tablet of claim 15, wherein the dosage form provides a minimum blood serum level of nalbuphine observed during the plateau that is not more than 25% below the mean blood serum level for all time points in the plateau.

19. The sustained release oral tablet of claim 15, wherein the minimum blood serum level is not more than 20% below the mean blood serum level for all time points in the plateau.

20. The sustained release oral tablet of claim 1, further comprising an enteric coating or a hydrophilic coating.

21. The sustained release oral tablet of claim 1, wherein the sustained release delivery system comprises a hydrophilic compound that forms a gel matrix.

22. A sustained release oral tablet, comprising from about 1 mg to about 200 mg nalbuphine or a pharmaceutically acceptable salt thereof in a sustained release matrix delivery system, the tablet providing an onset of nalbuphine effect from about 30 minutes of dosing to within about 6 hours of dosing and a duration of nalbuphine effect of at least 8 hours.

23. The dosage form of claim 22, which provides a $C_{max}$ from about 1.95 to about 102.00 ng/ml in a healthy human subject.

24. The dosage form of claim 23, which provides a Tmax at about 1.00 hour to about 16 hours after administration of the dosage form to a healthy human subject.

* * * * *